United States Patent
Watanabe et al.

(10) Patent No.: US 7,877,238 B2
(45) Date of Patent: Jan. 25, 2011

(54) DATA CLASSIFICATION SUPPORTING METHOD, COMPUTER READABLE STORAGE MEDIUM, AND DATA CLASSIFICATION SUPPORTING APPARATUS

(75) Inventors: Kiyoaki Watanabe, Tokyo (JP); Yohko Kawai, Tokyo (JP); Takayuki Mitsuhashi, Sagamihara (JP); Dai Furuie, Kobe (JP); Minoru Okamoto, Kobe (JP)

(73) Assignee: Sysmex Corporation (JP)

( * ) Notice: Subject to any disclaimer, the term of this patent is extended or adjusted under 35 U.S.C. 154(b) by 399 days.

(21) Appl. No.: 10/938,116

(22) Filed: Sep. 10, 2004

(65) Prior Publication Data

US 2005/0060329 A1    Mar. 17, 2005

(30) Foreign Application Priority Data

| Sep. 12, 2003 | (JP) | 2003-320829 |
| Sep. 12, 2003 | (JP) | 2003-320833 |
| Sep. 12, 2003 | (JP) | 2003-320848 |
| Sep. 12, 2003 | (JP) | 2003-320851 |

(51) Int. Cl.
*G06F 17/10* (2006.01)
*G06F 7/60* (2006.01)

(52) U.S. Cl. .................. 703/2; 702/19; 703/11; 706/20

(58) Field of Classification Search .............. None
See application file for complete search history.

(56) References Cited

U.S. PATENT DOCUMENTS

| 6,278,799 B1 * | 8/2001 | Hoffman | 382/159 |
| 2003/0158828 A1 * | 8/2003 | Ikeda et al. | 706/12 |
| 2003/0233197 A1 * | 12/2003 | Padilla et al. | 702/20 |

FOREIGN PATENT DOCUMENTS

| JP | 2003-006211 A | 1/2003 |
| JP | 2003-044828 A | 2/2003 |
| JP | 2003-122844 A | 4/2003 |

* cited by examiner

*Primary Examiner*—Carolyn L. Smith
(74) *Attorney, Agent, or Firm*—Brinks Hofer Gilson & Lione

(57) ABSTRACT

A data classification supporting method capable of easily discriminating a cell to which unknown data belongs and cells similar to the unknown data from each other is obtained. This classification compares cell vector data of each cell with the unknown data, decides a cell having cell vector data closest to the unknown data and cells having cell vector data secondly to nthly close to the unknown data as a minimum cell and similar cells respectively and displays a minimum cell mark and similar cell marks indicating the minimum cell and the similar cells respectively on a classification map.

10 Claims, 11 Drawing Sheets

FIG.4

[SCREEN 3] SPECIMEN DATA SELECTION POPUP SCREEN

☐ PATIENT DATA ADDITIONAL SCREEN
SELECT PATIENT DATA FILE

[READ FILE] — 31

| | | WBC | RBC | HGB | HCT | MCV | MCH | MCHC |
|---|---|---|---|---|---|---|---|---|
| 271 | ALL | 5.4 | 2.18 | 6.4 | 20.4 | 94 | 29.4 | 31.4 |
| 183 | ALL(B-ALL) | 1.6 | 2.57 | 8.2 | 23.9 | 93 | 31.9 | 34.3 |
| 185 | ALL(T-ALL) | 11 | 5.39 | 15.4 | 45 | 84 | 28.6 | 34.2 |
| 180 | ALL:B | 8.4 | 5.13 | 13.5 | 41 | 80 | 26.3 | 32.9 |
| 158 | ALL(B-ALL) | 8.4 | 5.13 | 13.5 | 41 | 80 | 26.3 | 32.9 |
| 159 | ALL(B-ALL) | 25.5 | 3.13 | 7.4 | 22.8 | 73 | 23.6 | 32.5 |
| 400 | ALL(B-ALL)co... | 112.6 | 2.11 | 5.7 | 17 | 81 | 27 | 33.5 |
| 212 | ALL(Bcell) | 8 | 2.3 | 6.6 | 20.8 | 90 | 28.7 | 31.7 |
| 175 | ALL:bipheno | 22 | 4.16 | 12.4 | 37.1 | 89 | 29.8 | 33.4 |
| 232 | ALL:bipheno | 47.1 | 4.7 | 11.6 | 37.8 | 80 | 24.7 | 30.7 |
| 443 | ALL(bipheno) | 2.1 | 3.17 | 8.7 | 27.2 | 86 | 27.4 | 32 |
| 1 | ALL,L1(B-ALL) | 12 | 3.82 | 9.7 | 29.5 | 77 | 25.4 | 32.9 |
| 2 | ALL,L1(B-ALL) | 2.7 | 1.72 | 4.8 | 13.2 | 77 | 27.9 | 36.4 |
| 3 | ALL,L1(B-ALL) | 60.9 | 3.22 | 8 | 25 | 78 | 24.8 | 32 |
| 4 | ALL,L1(B-ALL) | 5.3 | 4.37 | 10.6 | 34.4 | 79 | 24.2 | 30.8 |
| 5 | ALL,L1(B-ALL) | 33.8 | 3.23 | 12 | 35 | 108 | 37.2 | 34.3 |
| 9 | ALL,L1(B-ALL) | 13 | 5.53 | 14.5 | 42.4 | 77 | 26.2 | 34.2 |
| 11 | ALL,L1(B-ALL) | 538 | 2.36 | 6.4 | 21.9 | 93 | 27.1 | 29.2 |
| 13 | ALL,L1(B-ALL) | 7.2 | 3.9 | 12.4 | 35.2 | 90 | 31.8 | 35.2 |
| 169 | ALL,L1(B-ALL) | 14.5 | 2.84 | 7.7 | 23.2 | 82 | 27.1 | 33.2 |
| 6 | ALL,L1(bipheno) | 15.5 | 3.26 | 10.6 | 32.3 | 99 | 32.4 | 32.7 |
| 7 | ALL,L1(bipheno) | 43.7 | 2.44 | 7.2 | 21.7 | 89 | 29.5 | 33.2 |
| 8 | ALL,L1(bipheno) | 6.4 | 1.7 | 4.9 | 15 | 88 | 28.9 | 32.8 |
| 12 | ALL,L1(bipheno) | 3.4 | 0.66 | 2.3 | 6.7 | 101 | 35.1 | 34.9 |
| 14 | ALL,L1(pH1+):b... | 121.5 | 5.32 | 16.4 | 46.3 | 87 | 30.9 | 35.4 |

DATA CLASSIFICATION SUPPORTING METHOD, COMPUTER READABLE STORAGE MEDIUM, AND DATA CLASSIFICATION SUPPORTING APPARATUS

This application claims priority under 35 U.S.C. §119 to Japanese Patent Application Nos. 2003-320829, 2003-320833, 2003-320848 and 2003-320851 all filed Sep. 12, 2003, the entire contents of which are hereby incorporated herein by reference.

BACKGROUND

The present invention relates to a method of and an apparatus for supporting data classifying, a program and a recording medium recording the program, and more particularly, it relates to a method of and an apparatus for supporting data classifying for arranging unknown data on any cell with a classification map consisting of an aggregate of a plurality of cells, a program and a recording medium recording the program.

A data classification supporting method for arranging unknown data on any cell with a classification map consisting of an aggregate of a plurality of cells is known in general. A self-organizing map (SOM) proposed by T. Kohonen, for example, is known as a classification map employed for this data classification supporting method. The data classification supporting method with the self-organizing map (SOM) treats unknown data as a multi-dimensional vector for classifying the unknown data to belong to a cell having high similarity with a self-organizing algorithm and displaying the same on a two-dimensional self-organizing map (refer to Japanese Patent Laying-Open No. 2003-44828, for example).

The above Japanese Patent Laying-Open No. 2003-44828 discloses a method of deciding a display position for unknown data of a multi-dimensional vector on a position deviating from a neuron (cell) to which the unknown data belongs on the basis of the distance between the neuron (cell) to which the unknown data belongs or a neuron (cell) in the vicinity thereof and the unknown data in a multi-dimensional vector space when displaying the unknown data on a two-dimensional self-organizing map plane with a self-organizing map. Thus, each unknown data can be identifiably displayed according to the method disclosed in Japanese Patent Laying-Open No. 2003-44828, also when the self-organizing map has only a small number of neurons (cells).

According to the method disclosed in Japanese Patent Laying-Open No. 2003-44828, however, it may be difficult to discriminate a neuron (cell) to which unknown data belongs and a neuron (cell) similar to the unknown data from each other since this method does not display which neuron (cell) is the neuron (cell) to which the unknown data belongs and which neuron (cell) is the neuron (cell) similar to the unknown data.

SUMMARY OF THE INVENTION

The scope of the present invention is defined solely by the appended claims, and is not affected to any degree by the statements within this summary.

A method of and an apparatus for supporting data classifying, a program and a recording medium recording the program according to the present invention simplify classifying of unknown data.

A data classification supporting method according to a first aspect of the present invention is a data classification supporting method for classifying unknown data on any cell with a classification map comprising a plurality of cells having cell vector data decided on the basis of prescribed learning data, and comprises steps of comparing the cell vector data of each cell with the unknown data, deciding the cells having the cell vector data firstly to nthly (n: integer of at least 2) close to the unknown data on the basis of results of the comparison between the cell vector data and the unknown data and displaying a minimum cell mark indicating a minimum cell and a similar cell mark indicating similar cell on the classification map while deciding the cell having the cell vector data firstly close to the unknown data as the minimum cell and deciding the cell having the cell vector data secondly to nthly close to the unknown data as the similar cell.

In the data classification supporting method according to the first aspect, as hereinabove described, the minimum cell mark indicating the minimum cell and the similar cell mark indicating the similar cell are displayed on the classification map while deciding the cell having the cell vector data firstly close to the unknown data and the cell having the cell vector data secondly to nthly close to the unknown data as the minimum cell and the similar cell respectively, whereby the minimum cell having the cell vector data firstly close to the unknown data and the similar cell having the cell vector data secondly to nthly close to the unknown data respectively can be easily visually recognized.

The aforementioned data classification supporting method according to the first aspect preferably further comprises a step of setting the number n to any integer of at least 2. According to this structure, the display range for the similar cells can be easily set.

In the aforementioned data classification supporting method according to the first aspect, the minimum cell mark and the similar cell mark preferably have different shapes. According to this structure, the difference between the minimum cell and the similar cells can be easily visually identified.

In the aforementioned data classification supporting method according to the first aspect, the minimum cell mark and the similar cell mark preferably have different colors. According to this structure, the difference between the minimum cell and the similar cells can be easily visually identified.

In the aforementioned data classification supporting method according to the first aspect, the similar cell mark is preferably expressed with line, and the thicknesses of the line correspond to the distance between the cell vector data secondly to nthly close to the unknown data and the unknown data. According to this structure, which one of the similar cells is close can be easily visually identified.

In the aforementioned data classification supporting method according to the first aspect, the unknown data is preferably clinical laboratory test data. According to this structure, the clinical laboratory test data can be classified with a classification map classified to prescribed diseases.

In the data classification supporting method according to the first aspect, the classification map is preferably a self-organizing map. According to this structure, the cells having the cell vector data firstly to nthly (n: integer of at least 2) close to the unknown data can be easily decided with the self-organizing map.

In the aforementioned data classification supporting method according to the first aspect, the step of displaying the minimum cell mark and the similar cell mark on the classification map preferably further includes a step of changing the classification map for centering the minimum cell mark on the classification map. According to this structure, the relation between the minimum cell mark and the similar cell marks located around the same can be more easily visually recognized.

A program for executing a data classification supporting method according to a second aspect of the present invention is a program for making a computer execute a data classification supporting method for classifying unknown data on any cell with a classification map comprising a plurality of cells having cell vector data decided on the basis of prescribed learning data, and comprises instructions executed on the computer to compare the cell vector data of each the cell with the unknown data, decide the cells having the cell vector data firstly to nthly (n: integer of at least 2) close to the unknown data on the basis of results of the comparison between the cell vector data and the unknown data and display a minimum cell mark indicating a minimum cell and a similar cell mark indicating similar cell on the classification map while deciding the cell having the cell vector data firstly close to the unknown data as the minimum cell and deciding the cell having the cell vector data secondly to nthly close to the unknown data as the similar cell.

In the program for executing the data classification supporting method according to the second aspect, as hereinabove described, the minimum cell mark indicating the minimum cell and the similar cell mark indicating the similar cell are displayed on the classification map while deciding the cell having the cell vector data firstly close to the unknown data and the cell having the cell vector data secondly to nthly close to the unknown data as the minimum cell and the similar cell respectively, whereby the minimum cell having the cell vector data firstly_ close to the unknown data and the similar cell having the cell vector data secondly to nthly close to the unknown data respectively can be easily visually recognized.

In this case, a machine-readable recording medium recording the aforementioned program according to the second aspect is preferably employed.

An data classification supporting apparatus according to a third aspect of the present invention is a data classification supporting apparatus for classifying unknown data on any cell with a classification map comprising a plurality of cells having cell vector data decided on the basis of prescribed learning data, and comprises comparison means comparing the cell vector data of each cell with the unknown data, decision means deciding the cells having the cell vector data firstly to nthly (n: integer of at least 2) close to the unknown data on the basis of results of the comparison between the cell vector data and the unknown data and display means displaying a minimum cell mark indicating a minimum cell and a similar cell mark indicating similar cell on the classification map while deciding the cell having the cell-vector data firstly close to the unknown data as the minimum cell and deciding the cell having the cell vector data secondly to nthly close to the unknown data as the similar cell.

As hereinabove described, the data classification supporting apparatus according to the third aspect is provided with the display means displaying the minimum cell mark indicating the minimum cell and the similar cell mark indicating the similar cell on the classification map while deciding the cell having the cell vector data firstly close to the unknown data as the minimum cell and deciding the cell having the cell vector data secondly to nthly close to the unknown data as the similar cell, whereby the minimum cell having the cell vector data firstly close to the unknown data and the similar cell having the cell vector data secondly to nthly close to the unknown data can be easily visually recognized.

A data classification supporting method according to a fourth aspect of the present invention is a data classification supporting method for classifying, unknown data on any cell with a classification map comprising a plurality of classification areas each including a plurality of cells having cell vector data decided on the basis of prescribed learning data, and comprises steps of comparing the cell vector data of each cell with the unknown data, deciding a minimum cell having the cell vector data closest to the unknown data on the basis of results of the comparison between the cell vector data and the unknown data and creating a first distribution chart of the learning data corresponding to the cells of the classification area to which the minimum cell belongs for clarifying the position of the unknown data on the first distribution chart.

In the data classification supporting method according to the fourth aspect, as hereinabove described, the first distribution chart of the learning data of the respective cells of the classification area to which the minimum cell belongs is created for clarifying the position of the unknown data on the first distribution chart, whereby whether or not a result of classifying of the unknown data is correct can be easily inferred from the positional relation between the unknown data and the first distribution chart. When the first distribution chart is created every element constituting the unknown data, the unknown data (specimen data) and the first distribution chart can be compared with each other every element, whereby the relation between the unknown data and the classification area to which the minimum cell belongs can be more correctly visually recognized.

The aforementioned data classification supporting method according to the fourth aspect preferably further comprises steps of deciding a similar cell having the cell vector data secondly to nthly (n: integer of at least 2) close to the unknown data on the basis of results of the comparison and creating a second distribution chart of the learning data corresponding to the minimum cell and the similar cells for clarifying the positional relation between the second distribution chart and the first distribution chart. According to this structure, whether or not a result of classifying of the unknown data is correct can be more easily inferred from the positional relation between the unknown data and the first and second distribution charts.

The aforementioned data classification supporting method according to the fourth aspect preferably further comprises a step of creating a third distribution chart of the learning data corresponding to the cells of the classifying area to which the minimum cell does not belong for clarifying the positional relation between the third distribution chart and the first distribution chart. According to this structure, whether or not the result of classifying of the unknown data is correct can be more easily inferred from the positional relation between the unknown data and the first and third distribution charts.

The aforementioned data classification supporting method according to the fourth aspect preferably further comprises a step of numerically displaying the unknown data. According to this structure, the unknown data can be not only visually but also numerically recognized.

The aforementioned data classification supporting method according to the fourth aspect preferably further comprises a step of numerically displaying the learning data corresponding to the minimum cell when the learning data corresponding to the minimum cell is present. According to this structure, the unknown data and the learning data corresponding to the minimum cell can be numerically compared with each other when the unknown data is numerically displayed, whereby whether or not the result of classifying of the unknown data is correct can be easily inferred along with the aforementioned comparison according to the first distribution chart.

In this case, the data classification supporting method preferably further comprises a step of numerically displaying the learning data corresponding to a similar cell secondly to nthly (n: integer of at least 2) close to the unknown data when the learning data corresponding to any of the similar cells secondly to nthly close to the unknown data is present. According to this structure, the unknown data and a prescribed number of close learning data present on the minimum cell and the similar cell secondly to nthly close to the unknown data can be numerically compared with each other, whereby whether or not the result of classifying of the unknown data is correct can be more easily inferred along with the aforementioned comparison according to the first distribution chart.

In the aforementioned data classification supporting method according to the fourth aspect, the learning data is preferably constituted of a vector consisting of a plurality of elements, and the step of creating the first distribution chart preferably includes a step of creating the first distribution chart as to the element constituting the learning data. According to this structure, the unknown data and the first distribution chart can be compared with each other as to each element constituting the learning data, whereby the relation between the unknown data and the classification area to which the minimum cell belongs can be more correctly visually recognized.

In the aforementioned data classification supporting method according to the fourth aspect, the first distribution chart is preferably displayed when the corresponding classification map is selected. According to this structure, the first distribution chart and the selected classification map can be displayed side by side, whereby whether or not the result of classifying of the unknown data is correct can be easily inferred.

In the data classification supporting method according to the fourth aspect, the unknown data is preferably clinical laboratory test data. According to this structure, whether or not a result of classifying of the clinical laboratory test data is correct can be easily inferred when classifying the clinical laboratory test data with a classification map classified for prescribed diseases according to the first distribution chart. Further, the relation between specimen data (unknown data) and the name of a disease (classification area) to which the minimum cell belongs can be more correctly visually recognized according to the first distribution chart created every element.

In the aforementioned data classification supporting method according to the fourth aspect, the classification map is preferably a self-organizing map. According to this structure, the minimum cell having the cell vector data closest to the unknown data can be easily decided according to the self-organizing map.

A program for executing a data classification supporting method according to a fifth aspect of the present invention is a program for making a computer execute a data classification supporting method for classifying unknown data on any cell with a classification map comprising a plurality of classification areas each including a plurality of cells having cell vector data decided on the basis of prescribed learning data, and comprises instructions executed on the computer to compare the cell vector data of each cell with the unknown data, decide a minimum cell having the cell vector data closest to the unknown data on the basis of results of the comparison between the cell vector data and the unknown data and create a first distribution chart of the learning data corresponding to the cells of the classification area to which the minimum cell belongs for clarifying the position of the unknown data on the first distribution chart.

In the program for executing a data classification supporting method according to the fifth aspect, as hereinabove described, the first distribution chart of the learning data of each cell of the classification area to which the minimum cell having the cell vector data closest to the unknown data belongs is created for clarifying the position of the unknown data on the first distribution chart, whereby whether or not a result of classifying of the unknown data is correct can be easily inferred from the positional relation between the unknown data and the first distribution chart. When the first distribution chart is created every element constituting the unknown data, the unknown data (specimen data) and the first distribution chart can be compared with each other every element, whereby the relation between the unknown data and the classification area to which the minimum cell belongs can be more correctly visually recognized.

In this case, a machine-readable recording medium recording the aforementioned program according to the fifth aspect is preferably employed.

An data classification supporting apparatus according to a sixth aspect of the present invention is a data classification supporting apparatus for classifying unknown data on any cell with a classification map comprising a plurality of classification areas each including a plurality of cells having cell vector data decided on the basis of prescribed learning data, comprising, and comprises comparison means comparing the cell vector data of each cell with the unknown data, minimum cell decision means deciding a minimum cell having the cell vector data closest to the unknown data on the basis of results of the comparison between the cell vector data and the unknown data and first distribution chart creation means creating a first distribution chart of the learning data corresponding to the cells of the classification area to which the minimum cell belongs for clarifying the position of the unknown data on the first distribution chart.

As hereinabove described, the data classification supporting apparatus according to the sixth aspect is provided with the first distribution chart creation means creating the first distribution chart of the learning data of each cell of the classification area to which the minimum cell having the cell vector data closest to the unknown data for clarifying the position of the unknown data on the first distribution chart, whereby whether or not a result of classifying of the unknown data is correct can be easily inferred from the positional relation between the unknown data and the first distribution chart. When the first distribution chart is created every element constituting the unknown data, the unknown data (specimen data) and the first distribution chart can be compared with each other every element, whereby the relation between the unknown data and the classification area to which the minimum cell belongs can be more correctly visually recognized.

A data classification supporting method according to a seventh aspect of the present invention is a data classification supporting method for classifying unknown data on any cell with a classification map comprising a plurality of classification areas each including a plurality of cells having cell vector data decided on the basis of prescribed learning data, and comprises steps of calculating a possibility that the unknown data belongs to a prescribed classification area and outputting the calculated possibility.

In the data classification supporting method according to the seventh aspect, as hereinabove described, the possibility that the unknown data belongs to the prescribed classification area is calculated and thereafter output so that with what degree of possibility the unknown data belongs to the prescribed classification area can be easily recognized.

In the aforementioned data classification supporting method according to the seventh aspect, the step of calculating the possibility preferably includes a step of calculating the possibility on the basis of the unknown data and the learning data corresponding to the cells belonging to the classification map. According to this structure, the possibility that the unknown data belongs to the prescribed classification map can be easily calculated. Further, a more correct possibility can be calculated by calculating the possibility on the basis of the unknown data.

The aforementioned data classification supporting method according to the seventh aspect may further include steps of comparing the cell vector data of each cell with the unknown data and deciding a minimum cell having the cell vector data closest to the unknown data on the basis of results of the comparison between the cell vector data and the unknown data.

In the aforementioned data classification supporting method according to the seventh aspect, the step of calculating the possibility preferably includes a step of calculating the possibility on the basis of the cell vector data of the minimum cell and the learning data corresponding to the cells belonging to the classification map. Also when calculating the possibility on the basis of the cell vector data of the minimum cell, the possibility that the unknown data belongs to the prescribed classification map can be easily calculated.

In the aforementioned data classification supporting method according to the seventh aspect, the step of calculating the possibility preferably, includes steps of calculating a first value on the basis of either the unknown data or the cell vector data of the minimum cell and the learning data corresponding to each cell belonging to the prescribed classification area, calculating a second value by summating values calculated on the basis of either the unknown data or the cell vector data of the minimum cell and the learning data corresponding to each cell belonging to any of the plurality of classification areas as to all of the plurality of classification areas and calculating the possibility by obtaining the ratio of the first value to the second value. According to this structure, the possibility that the unknown data belongs to the prescribed classification area can be easily calculated according to the ratio of the first value to the second value.

In the aforementioned data classification supporting method according to the seventh aspect, the step of calculating the possibility preferably includes a step of calculating the possibility with an expression including a function reaching a larger value as the inter-vector distance between either the unknown data or the cell vector data of the minimum cell and the learning data is reduced. According to this structure, the value indicating the possibility is increased as the inter-vector distance between either the unknown data or the cell vector data of the minimum cell and the learning data is reduced, whereby the possibility can be correctly calculated. In this case, the function preferably includes a Gaussian function. According to this structure, the value indicating the possibility can be easily increased as the inter-vector distance between either the unknown data or the cell vector data of the minimum cell and the learning data is reduced.

In the aforementioned data classification supporting method according to the seventh aspect, the step of calculating the possibility preferably includes a step of calculating a possibility Eic that the unknown data belongs to the prescribed classification area c according to the following expression:

$$Eic = Kc/K$$

on the basis of the values Kc and K obtained as follows:

$$Kc = \sum_{j=1}^{Nc} \frac{1}{Nc} \cdot f(|Ei - Scj|)$$

$$K = \sum_{c=1}^{M} Kc$$

where Nc represents the number of learning data in the classification area c, M represents the number of the classification areas, Scj represents j-th learning data belonging to the classification area c, Ei represents the unknown data or the cell vector data of the minimum cell, and f( ) represents the Gaussian function. According to this structure, the possibility can be easily calculated according to the above expression.

In the aforementioned data classification supporting method according to the seventh aspect, the unknown data is preferably clinical laboratory test data. According to this structure, with what degree of possibility the clinical laboratory test data belongs to a prescribed disease (classification area) can be easily recognized.

In the aforementioned data classification supporting method according to the seventh aspect, the classification map is preferably a self-organizing map. According to this structure, the minimum cell having the cell vector data closest to the unknown data can be easily decided according to the self-organizing map.

A program for making a computer execute a data classification supporting method according to an eighth aspect of the present invention is a program for making a computer execute a data classification supporting method for classifying unknown data on any cell with a classification map comprising a plurality of classification areas each including a plurality of cells having cell vector data decided on the basis of prescribed learning data, and comprises instructions executed on the computer to calculate a possibility that the unknown data belongs to a prescribed classification area and output the calculated possibility.

In the program for making a computer execute a data classification supporting method according to the eighth aspect, as hereinabove described, the possibility that the unknown data belongs to the prescribed classification area is calculated and thereafter output so that with what degree of possibility the unknown data belongs to the prescribed classification area can be easily recognized.

In this case, a machine-readable recording medium recording the aforementioned program according to the eighth aspect is preferably employed.

An data classification supporting apparatus according to a ninth aspect of the present invention is a data classification supporting apparatus for classifying unknown data on any cell with a classification map comprising a plurality of classification areas each including of a plurality of cells having cell vector data decided on the basis of prescribed learning data, and comprises possibility calculation means calculating a possibility that the unknown data belongs to a prescribed classification area and output means outputting the calculated possibility.

As hereinabove described, the data classification supporting apparatus according to the ninth aspect is provided with the possibility calculation means calculating the possibility that the unknown data belongs to the prescribed classification area and the output means outputting the calculated possibility, whereby with what degree of possibility the unknown data belongs to the prescribed classification area can be easily recognized.

A data classification supporting method according to a tenth aspect of the present invention is a data classification supporting method for classifying unknown data on any cell with a classification map comprising a plurality of classification areas each including a plurality of cells having cell vector data decided on the basis of prescribed learning data, and comprises steps of arranging the unknown data on any cell with a first classification map including a first classification area and a second classification area, arranging the unknown data on any cell of a second classification map with the second classification map for further classifying the first classification area of the first classification map to which the cell having the unknown data arranged thereon belongs, and arranging the unknown data on any cell of a third classification map with the third classification map for further classifying the second classification area of the first classification map to which the cell having the unknown data arranged thereon does not belong.

In the data classification supporting method according to the tenth aspect, as hereinabove described, the unknown data is arranged on any cell of the second classification map with the second classification map for further classifying the first classification area of the first classification map to which the cell having the unknown data arranged thereon belongs while the unknown data is arranged on any cell of the third classification map with the third classification map for further classifying the second classification area of the first classification map to which the cell having the unknown data arranged thereon does not belong, so that the user can easily recognize that a result of classifying other than that of the second classification map may be obtained by the third classification map. Thus, the user can recognize that no correct result of classifying may be obtained.

The aforementioned data classification supporting method according to the tenth aspect may further comprises step of displaying the first classification map, the second classification map and the third classification map.

The aforementioned data classification supporting method according to the tenth aspect preferably further comprises steps of calculating a possibility that the unknown data belongs to the first classification area and the second classification area of the first classification map and displaying the calculated possibility. According to this structure, the user can visually recognize the possibility that the unknown data belongs to the first and second classification areas corresponding to the second and third classification maps respectively.

In the aforementioned data classification supporting method including the step of calculating the possibility, the magnitude of the possibility preferably corresponds to the thickness of a line connecting the first classification map and the second and third classification maps with each other. According to this structure, the user can easily visually recognize the possibility that the unknown data belongs to the second and third classification maps.

In the aforementioned data classification supporting method including the step of calculating the possibility, the magnitude of the possibility is preferably displayed by a numerical value showing a proportion. According to this structure, the user can numerically correctly recognize the possibility that the unknown data belongs to the second and third classification maps.

In the aforementioned data classification supporting method according to the tenth aspect, the second classification map preferably includes a third classification area, and the method preferably further comprises a step of calculating a possibility that the unknown data belongs to the third classification area of the second classification map. According to this structure, the user can numerically correctly recognize the possibility that the unknown data belongs to the third classification area of the second classification map.

In the aforementioned data classification supporting method according to the tenth aspect, the third classification map preferably includes a fourth classification area, and the method preferably further comprises a step of calculating a possibility that the unknown data belongs to the fourth classification area of the third classification map. According to this structure, the user can numerically correctly recognize the possibility that the unknown data belongs to the fourth classification area of the third classification map.

In the aforementioned data classification supporting method according to the tenth aspect, the unknown data is preferably clinical laboratory test data. According to this structure, the user can recognize that a result of classifying (disease name) other than that (disease name) of the second classification map may be obtained due to the display of the third classification map by classifying the clinical laboratory test data and displaying the first to third classification maps.

In the aforementioned data classification supporting method according to the tenth aspect, the classification map is preferably a self-organizing map. According to this structure, the minimum cell having the cell vector data closest to the unknown data can be easily decided according to the self-organizing map.

A program for making a computer execute a data classification supporting method according to an eleventh aspect of the present invention is a program for making a computer execute a data classification supporting method for classifying unknown data on any cell with a classification map comprising a plurality of classification areas each including a plurality of cells having cell vector data decided on the basis of prescribed learning data, and comprises instructions executed on the computer to arrange the unknown data on any cell with a first classification map including a first classification area and a second classification area, arrange the unknown data on any cell of a second classification map with the second classification map for further classifying the first classification area of the first classification map to which the cell having the unknown data arranged thereon belongs, and arrange the unknown data on any cell of a third classification map with the third classification map for further classifying the second classification area of the first classification map to which the cell having the unknown data arranged thereon does not belong.

In the program for making a computer execute a data classification supporting method according to the eleventh aspect, as hereinabove described, the unknown data is arranged on any cell of the second classification map with the second classification map for further classifying the first classification area of the first classification map to which the cell having the unknown data arranged thereon belongs while the unknown data is arranged on any cell of the third classification map with the third classification map for further classifying the second classification area of the first classification map to which the cell having the unknown data arranged thereon does not belong, so that the user can recognize that a result of classifying other than that of the second classification map may be obtained by the third classification map. Thus, the user can recognize that no correct result of classifying may be obtained.

In this case, a machine-readable recording medium recording the aforementioned program according to the eleventh aspect is preferably employed.

An data classification supporting apparatus according to a twelfth aspect of the present invention is a data classification supporting apparatus for classifying unknown data on any cell with a classification map comprising a plurality of classification areas each including a plurality of cells having cell vector data decided on the basis of prescribed learning data, and comprises first cell arranging means arranging the unknown data on any cell with a first classification map including a first classification area and a second classification area, second cell arranging means arranging the unknown data on any cell of a second classification map with the second classification map for further classifying the first classification area of the first classification map to which the cell having the unknown data arranged thereon belongs, and third cell arranging means arranging the unknown data on any cell of a third classification map with the third classification map for further classifying the second classification area of the first classification map to which the cell having the unknown data arranged thereon does not belong.

As hereinabove described, the data classification supporting apparatus according to the twelfth aspect is provided with the second cell arranging means arranging the unknown data on any cell of the second classification map with the second classification map for further classifying the first classification area of the first classification map to which the cell having the unknown data arranged thereon belongs, the third cell arranging means arranging the unknown data on any cell of the third classification map with the third classification map for further classifying the second classification area of the first classification map to which the cell having the unknown data arranged thereon does not belong, whereby the user can recognize that a result of classifying other than that of the second classification map may be obtained by the third classification map. Thus, the user can recognize that no correct result of classifying may be obtained.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 illustrates a specimen data selection screen (screen 3) in the data classification supporting method according to the embodiment of the present invention;

DETAILED DESCRIPTION OF THE EMBODIMENT

An embodiment of the present invention is now described with reference to the drawings. According to this embodiment, the present invention is applied to a case of classifying clinical laboratory test data (unknown data) to a prescribed disease (classification area).

An analytical result screen appearing on a display of a computer terminal (client) when classifying the clinical laboratory test data to the prescribed disease (classification area) with the data classification supporting method according to this embodiment is described with reference to FIGS. 1 to 3. This computer terminal (client), connected to a server (not shown), can be utilized after login with a registered user ID and a registered password.

Figure 1:
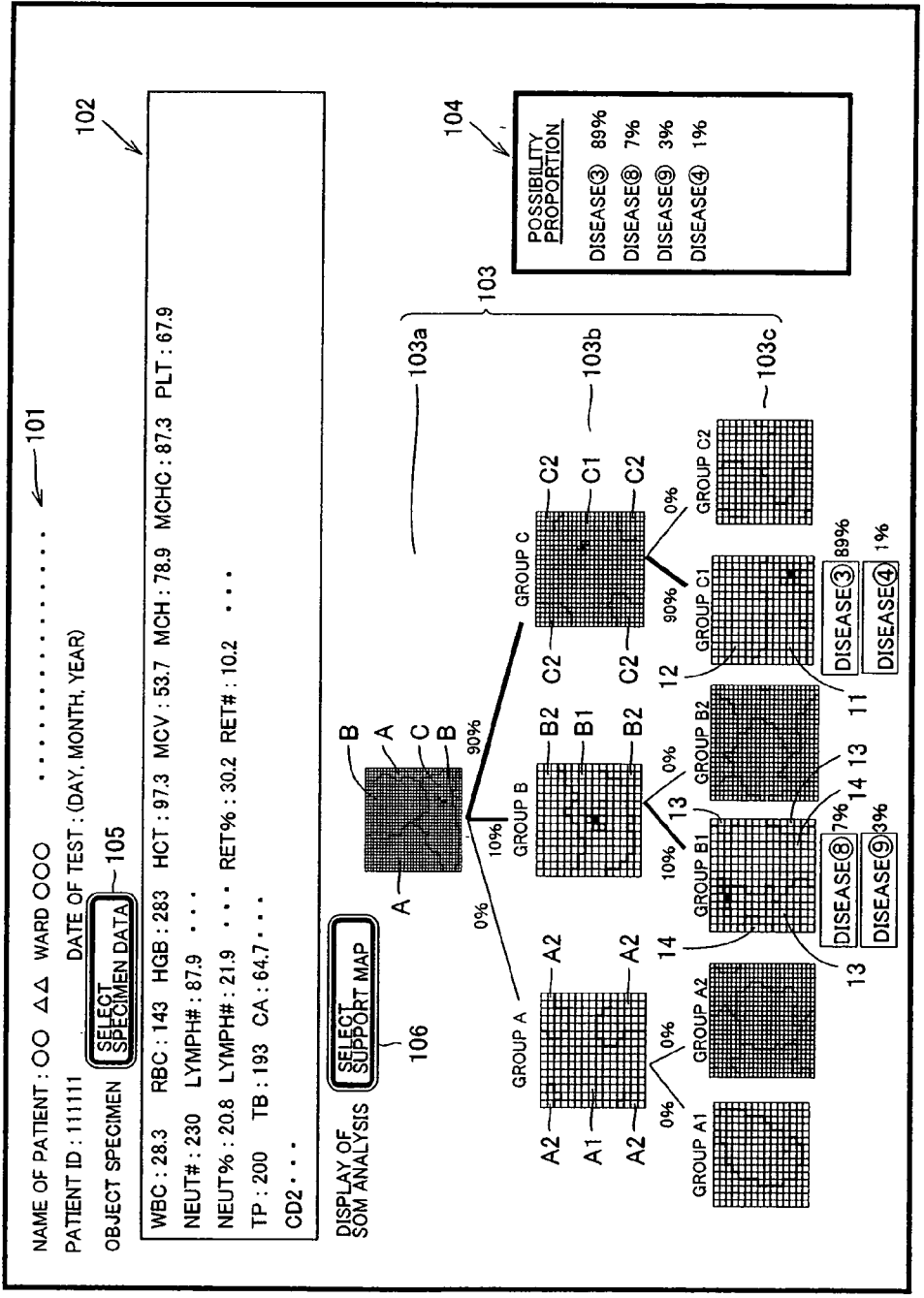
FIG. 1 illustrates an analytical result screen (screen 1) in a data classification supporting method according to an embodiment of the present invention.

The analytical result screen (screen 1) shown in FIG. 1 is provided with a patient attribute data display part 101 displaying attribute data for specifying a patient, a specimen data display part 102 displaying specimen data of the patient displayed on the patient attribute data display part 101, a self-organizing map display part displaying tree (hierarchical) self-organizing maps 103 and a disease possibility proportion display part 104 displaying final disease possibility proportions. FIG. 2 shows an analytical detail popup screen (screen 2-1) displayed when the user clicks a third-stage self-organizing map 103c of a group C1 of the self-organizing maps 103 tree-displayed (hierarchically displayed) on the analytical result screen (screen 1) shown in FIG. 1. FIG. 3 shows another analytical detail popup screen (screen 2-2) displayed when the user clicks a display switch (center) tab 107 of the analytical detail popup screen (screen 2-1) shown in FIG. 2. Referring to FIG. 2, an ignition cell (minimum cell) to which unknown data belongs is located on an end (lower right end) of the self-organizing map 103c of the group C1. Referring to FIG. 3, the ignition cell (minimum cell) to which the unknown data belongs is located at the center of the self-organizing map 103c of the group C1. The analytical detail popup screens shown in FIGS. 2 and 3 show histograms 20 and vector element values of an object specimen (unknown data) and similar specimens every element along with the self-organizing map 103c of the group C1. Elements 1, 2 and 3 are the leukocyte count, the erythrocyte count and the hemoglobin rate respectively. In the histogram 20 related to the element 1, the axes of abscissa and ordinate show the leukocyte count and the frequency respectively. In the histogram 20 related to the element 2, the axes of abscissa and ordinate show the erythrocyte count and the frequency respectively. In the histogram 20 related to the element 3, the axes of abscissa and ordinate show the hemoglobin rate and the frequency respectively. Clinical laboratory test data such as a hematocrit value and a mean cell volume (MCV) can be employed as other elements.

Figure 5:
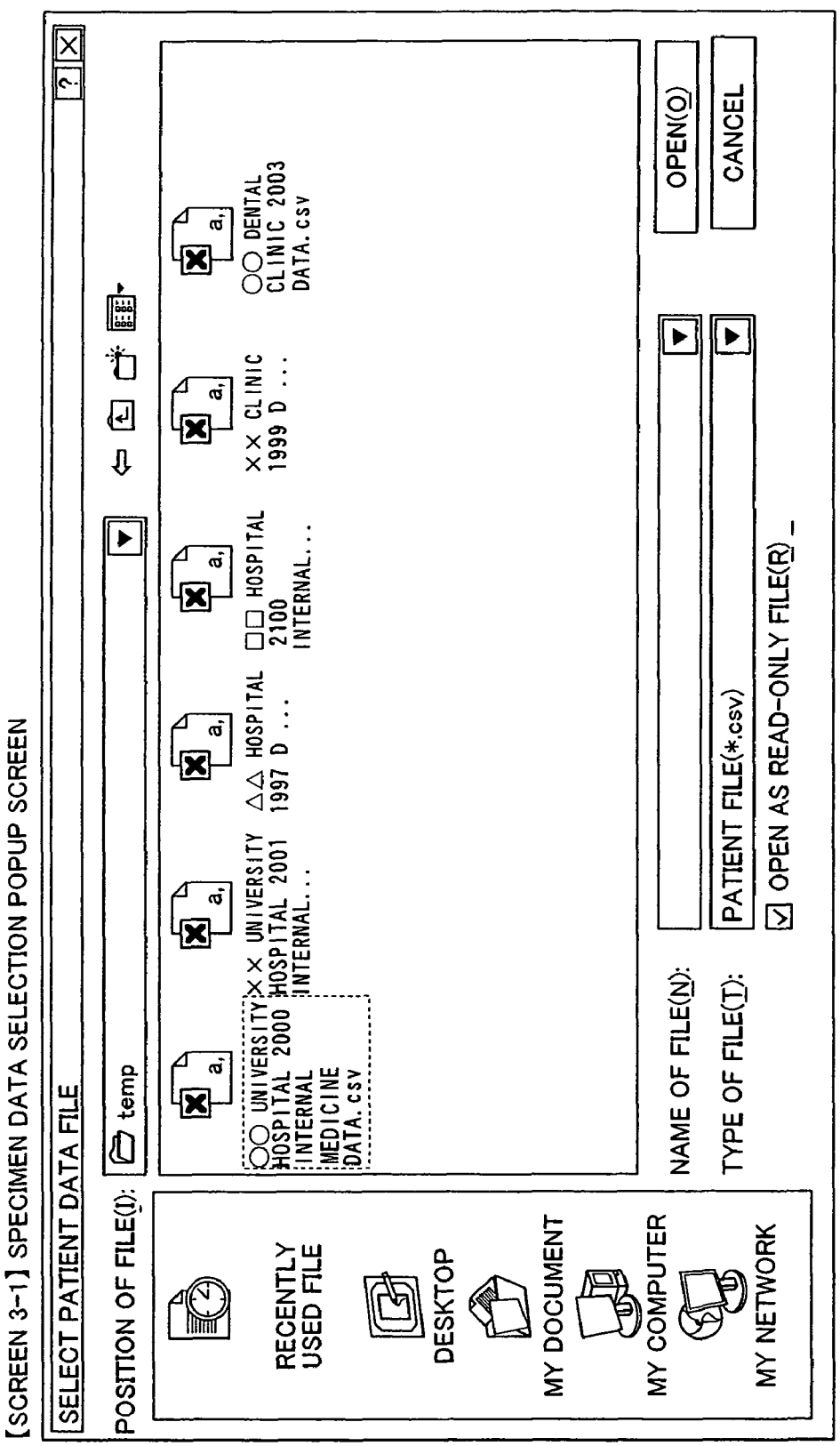
FIG. 5 illustrates a file read screen (screen 3-1) of the specimen data selection screen shown in FIG. 4.
Figure 6:
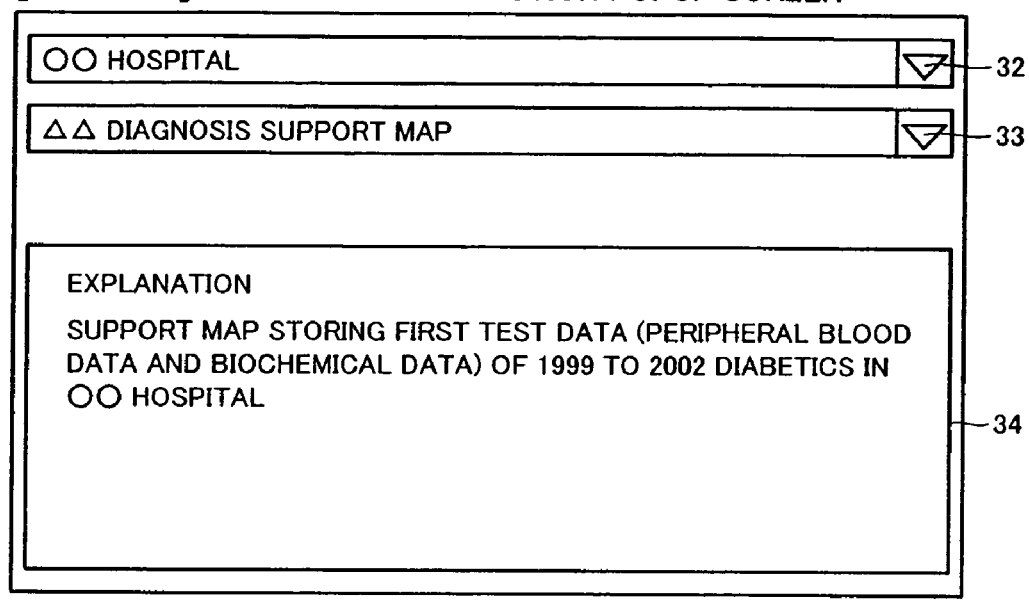
FIG. 6 illustrates a support map selection screen (screen 4) in the data classification supporting method according to the embodiment of the present invention.

FIG. 4 shows a specimen data selection popup screen (screen 3) displayed when the user clicks a specimen data selection tab 105 for selecting the specimen data (unknown data) on the analytical result screen (screen 1) shown in FIG. 1. FIG. 5 shows a specimen data selection popup screen (screen 3-1) displayed when the user clicks a file reading tab 31 of the specimen data selection popup screen (screen 3) shown in FIG. 4. FIG. 6 shows a support map selection popup screen displayed when the user clicks a support map selection tab 106 for selecting the used self-organizing map on the analytical result screen (screen 1) shown in FIG. 1.

The data classification supporting method according to this embodiment performed with the computer terminal (client) is now described with reference to FIGS. 1 to 13. Before performing the data classification supporting method described below, a recording medium such as an FD or a CD storing a program for executing the data classification supporting method according to this embodiment must be built into the computer terminal (client) or the server, or the program must be installed in the computer terminal (client) or the server from the aforementioned recording medium. A control part of the computer terminal or the server having the aforementioned recording medium built or installed therein executes the data classification supporting method according to this embodiment. The control part includes a memory such as a ROM or a RAM and a CPU. The memory stores the aforementioned program, input data and the like, and the CPU runs the aforementioned program.

In the data classification supporting method according to this embodiment, the user selects the corresponding self-organizing map (support map) for thereafter classifying the unknown data. More specifically, the user first clicks the support map selection tab 106 on the analytical result screen (screen 1) shown in FIG. 1, for opening the support map selection popup screen (screen 4) shown in FIG. 6. On this screen 4, the user selects a map creating facility in a server database (server DB) in a pull-down menu 32. Thus, self-organizing maps created by the facility are reflected on another pull-down menu 33. On the pull-down menu 33, the user selects a self-organizing map classified to a desired disease from the self-organizing maps of the facility selected in the pull-down menu 32. When the user selects the self-organizing map in the pull-down menu 33, an explanation display part 34 displays the explanation of the selected self-organizing map.

Figure 7:
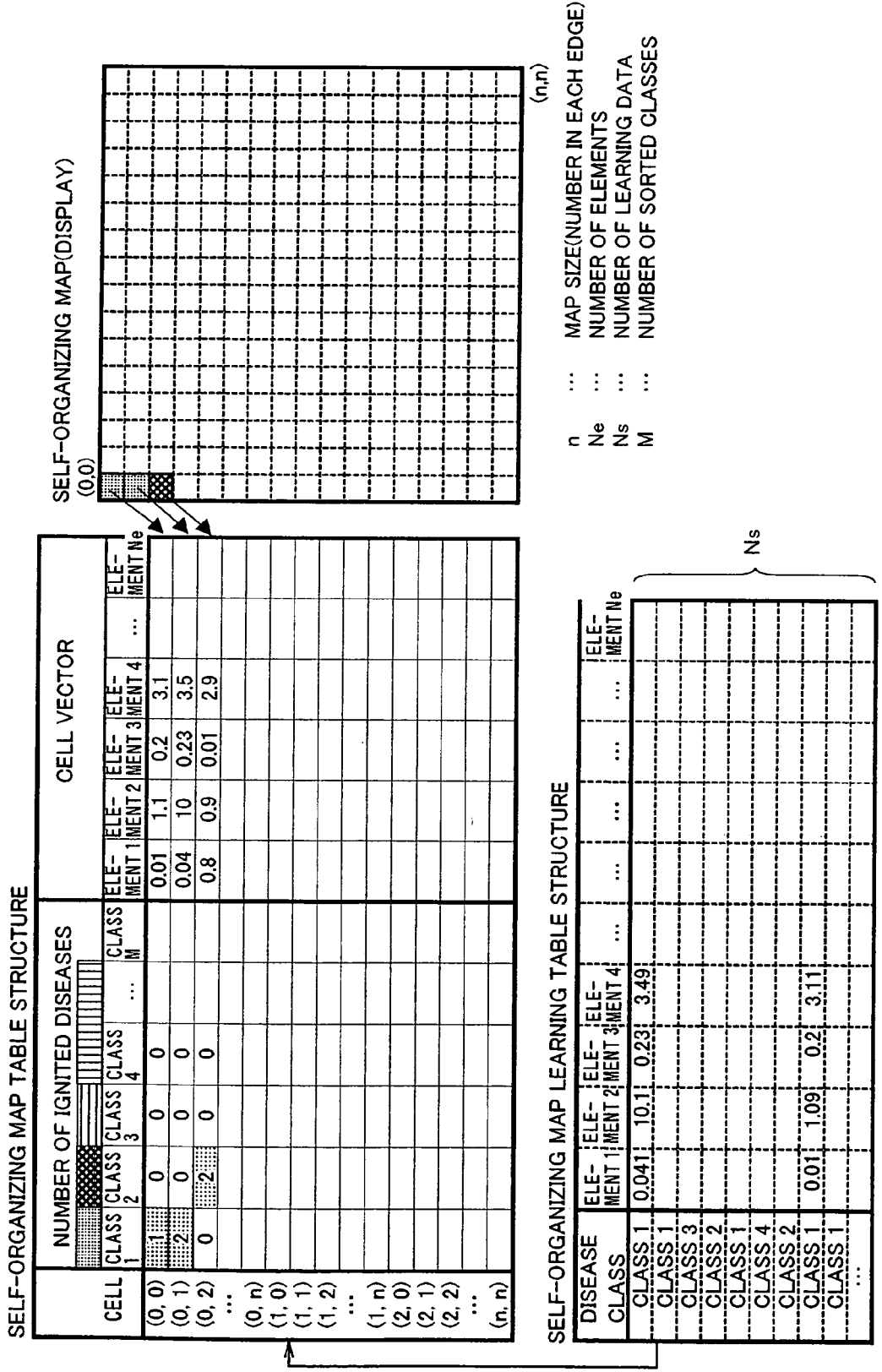
FIG. 7 illustrates a self-organizing map table structure in the data classification supporting method according to the embodiment of the present invention.

The self-organizing map employed in this embodiment is now described with reference to FIG. 7. The self-organizing map employed in this embodiment is created on the basis of a self-organizing map learning table structure and a self-organizing map table structure shown in FIG. 7. In the self-organizing map learning table structure shown in FIG. 7, each learning data is constituted of transversely arranged Ne (Ne-dimensional) elements 1 to Ne. The learning data are those of actual patients determined by doctors. FIG. 7 illustrates Ns learning data. FIG. 7 also shows disease names (classes 1 to M) actually determined by the doctors in correspondence to the respective learning data. On the basis of the respective learning data and the disease names (classes 1 to M) actually determined by the doctors in correspondence thereto, cell vector data and classes. (classification areas) to which the cell vector data belong are decided and displayed on a two-dimensional self-organizing map (refer to the upper right end of FIG. 7). This self-organizing map is constituted of n☐n=n2 cells. The term "cell vector data" indicates data obtained by learning the learning data with a self-organizing algorithm. The cell vector data of each cell is constituted of Ne (Ne-dimensional) elements 1 to Ne, similarly to the learning data. Each cell necessarily has cell vector data. On the other hand, each cell may or may not have learning data.

The self-organizing map shown in FIG. 7 is created by the prescribed facility and preserved in the server database (server DB). The user selects this self-organizing map on the screen 4 shown in FIG. 6.

After the user selects the support map (self-organizing map) on the screen 4 shown in FIG. 6, the specimen data (unknown data) is classified with this support map (self-organizing map). More specifically, the specimen data (unknown data) is first classified with a first-stage self-organizing map 103a (see FIG. 1) at a step 41. This classifying of the specimen data (unknown data) is described in detail with reference to FIGS. 9 and 10. The control part of the computer terminal or the server executes this specimen data classifying.

Figure 9:
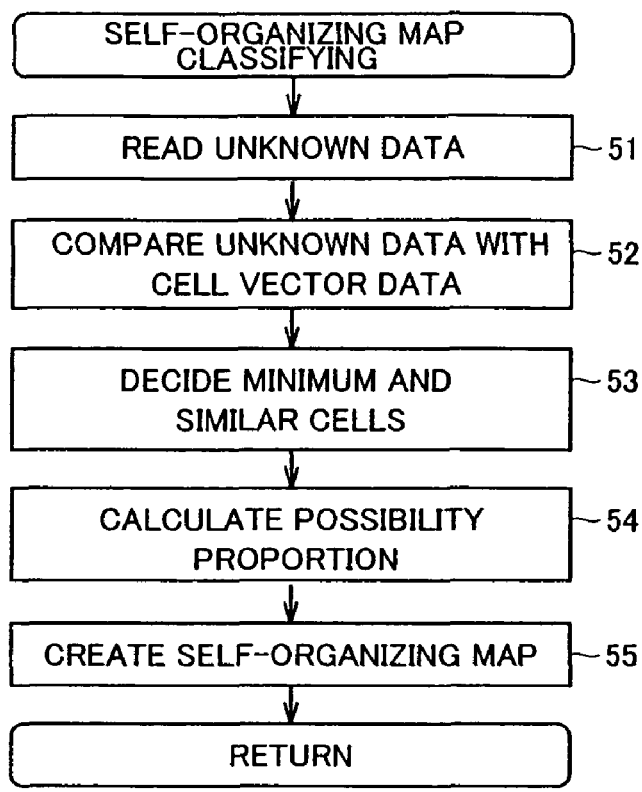
FIG. 9 is a flow chart for illustrating self-organizing map classifying in the data classification supporting method according to the embodiment of the present invention.

In the self-organizing map classifying according to this embodiment, the control part reads the unknown data (specimen data) at a step 51, as shown in FIG. 9. The user clicks the specimen data selection tab 105 on the analytical result screen (screen 1) shown in FIG. 1, so that the control part reads the unknown data (specimen data). More specifically, the user clicks the specimen data selection tab 105 on the screen 1 shown in FIG. 1, for displaying the specimen data selection popup screen (screen 3) shown in FIG. 4. The user clicks the file reading tab 31 on this screen 3 for opening the specimen data selection popup screen (screen 3-1) shown in FIG. 5. The user selects a prescribed specimen data file (CSV or XML (MML) file) for reading this file. Thus, the screen 3 shown in FIG. 4 displays a specimen data list of the read file. The user clicks a specimen to be analyzed in the specimen data list displayed on the screen 3, thereby selecting the specimen data. Thus, the screen 3 shown in FIG. 4 is closed and the specimen data display part 102 of the analytical result screen (screen 1) shown in FIG. 1 displays the read specimen data. The specimen data (unknown data) is constituted of Ne (Ne-dimensional) elements 1 to Ne, similarly to the aforementioned learning data and the aforementioned cell vector data.

After reading the specimen data (unknown data) at the step 51 shown in FIG. 9 as hereinabove described, the control part compares the unknown data (specimen data) with the cell vector data at a step 52.

According to this embodiment, the control part compares the unknown data (specimen data) with the cell vector data at the step 52 shown in FIG. 9, thereby deciding a cell (ignition cell) having cell vector data firstly close to the unknown data as a minimum cell while deciding cells having cell vector data secondly to nthly close to the unknown data as similar cells. The number n represents an integer of at least 2, which is set to 11 in this embodiment.

Thereafter the control part calculates possibility proportions at a step 54 shown in FIG. 9. The method of calculating the possibility proportions is now described. It is assumed that M represents the number of classes (classification areas) and Nc represents the number of learning data of a class (classification area) c. It is also assumed that Scj represents a j-th learning vector belonging to the class (classification area) c. The proportion value EiC of the class (classification area) c with respect to an i-th cell vector Ei is calculated as follows:

$$Eic = Kc/K$$

According to this embodiment, the unknown data (specimen data) is employed as the i-th cell vector Ei. The proportion values Eic as to all classes (classification areas) (c=1 to M) are obtained as class (classification area) proportion values of the unknown data (specimen data). The values Kc and K are obtained according to the following expressions (1) and (2):

$$Kc = \sum_{j=1}^{Nc} \frac{1}{Nc} \cdot f(|Ei - Scj|) \quad (1)$$

$$K = \sum_{c=1}^{M} Kc \quad (2)$$

In the above expression (1), a Gaussian function is utilized as f( ).

In the expression (1), the cell vector data of the minimum cell may be employed as the i-th cell vector Ei in place of the unknown data. Further, a delta function or the like may be employed as f( ) in place of the Gaussian function.

After calculating the possibility proportions at the step 54 shown in FIG. 9, the control part creates the self-organizing map at a step 55.

Figure 10:
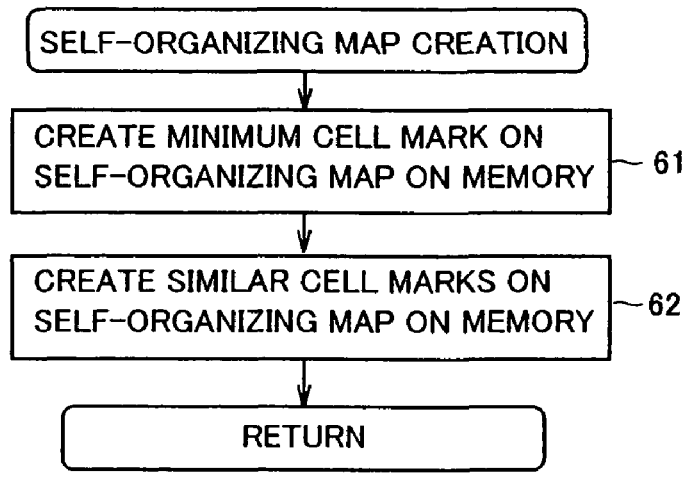
FIG. 10 is a flow chart for illustrating self-organizing map creation in the data classification supporting method according to the embodiment of the present invention.

In the procedure of creating the self-organizing map, the control part creates a minimum cell mark 1a on the self-organizing map of the memory at a step 61, as shown in FIG. 10. According to this embodiment, the control part employs a mark X indicating the point of a minimum cell 1 closest to the specimen data (unknown data) as the minimum cell mark 1a, as shown in FIG. 2. Further, the control part creates similar cell marks 2a indicating similar cells 2 secondly to nthly (eleventhly) close to the specimen data (unknown data) on the self map of the memory at a step 62. The control part employs squares (□) indicating the areas of respective similar cells 2 as the similar cell marks 2a, as shown in FIG. 2.

Figure 2:
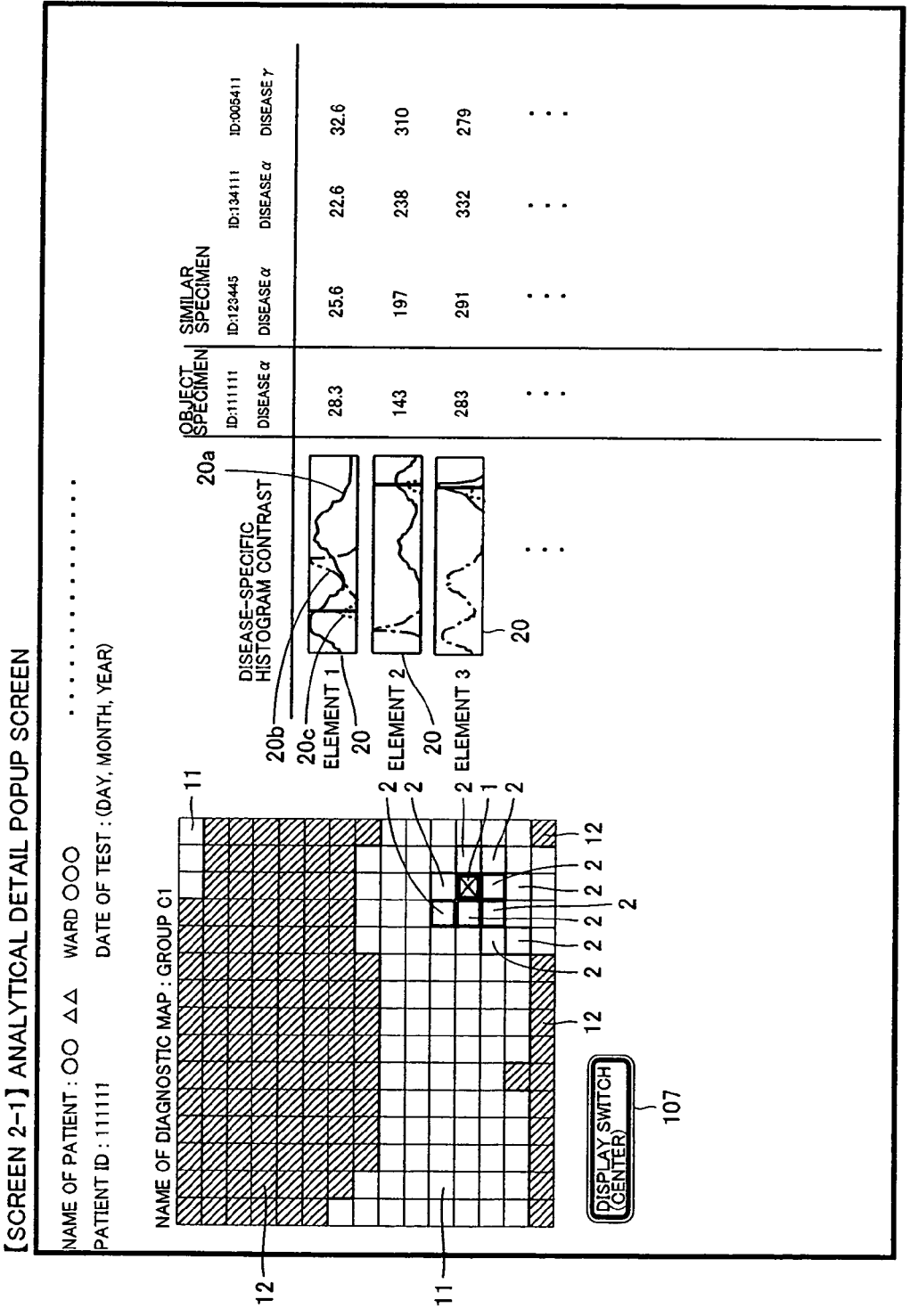
FIG. 2 illustrates an analytical detail screen (standard display) (screen 2-1) of the analytical result screen shown in FIG. 1.

According to this embodiment, the control part displays the minimum cell (ignition cell) 1 having the closest distance to the unknown data with the minimum cell mark 1a on the self-organizing map, as shown in FIG. 2. If the control part merely displays the coordinates of only one cell (minimum cell 1), however, the distance relation between the cell vector data of peripheral cells and the unknown data remains unclear. According to this embodiment, therefore, the control part displays the marks 1a and 2a of not only the minimum cell 1 having the closest distance to the unknown data but the similar cells 2, close to the unknown data, around the minimum cell 1. Thus, the control part can also visualize the relation between the unknown data (specimen data) and the similar cells 2. In this case, the control part varies the similar cell marks 2a with the distances between the unknown data and the cell vector data of the similar cells 2. More specifically, the control part reduces the thicknesses of the lines forming the squares (□) of the similar cell marks 2a as the distances between the unknown data and the cell vector data of the similar cells 2 are increased, as shown in FIG. 2. According to this embodiment, the control part displays the thinnest one of the lines forming the squares (□) of the similar cell marks 2a thicker than each frame line showing each cell area, thereby rendering the lines forming the squares (□) indicating the similar cell marks 2a distinguishable from the frame lines indicating the cell areas.

On a color-displayable screen, the control part can display the lines forming the squares (□) indicating the similar cell marks 2a distinguishably from the frame lines indicating the cell areas by differentiating the color of the former from that of the latter without differentiating the thicknesses thereof from each other. On the color-displayable screen, the control part preferably differentiates the color of the minimum cell mark 1a from those of the similar cell marks 2a and the frame lines indicating the cell areas.

The control part can also vary the areas of the cells 1 and 2 displayed by the minimum cell mark 1a and the similar cell marks 2a with a threshold S. More specifically, the control part calculates a distance L with the threshold S for displaying cells separated from the unknown data (specimen data) at distances smaller than the distance L as the minimum cell 1 and the similar cells 2. The control part calculates the distance L as follows:

L=average of inter-vector distance between all adjacent cells on the self-organizing map×S According to this embodiment, the threshold S is so set as to display the cells (the minimum cell 1 and the similar cells 2) firstly to eleventhly (nthly) close to the unknown data (specimen data) with the marks 1a and 2a respectively.

The control part creates the self-organizing map at the step 55 shown in FIG. 9 in the aforementioned manner. Thus, the control part completes the classifying of the specimen data (unknown data) with the first-stage self-organizing map 103a at the step 41 shown in FIG. 8.

Figure 8:
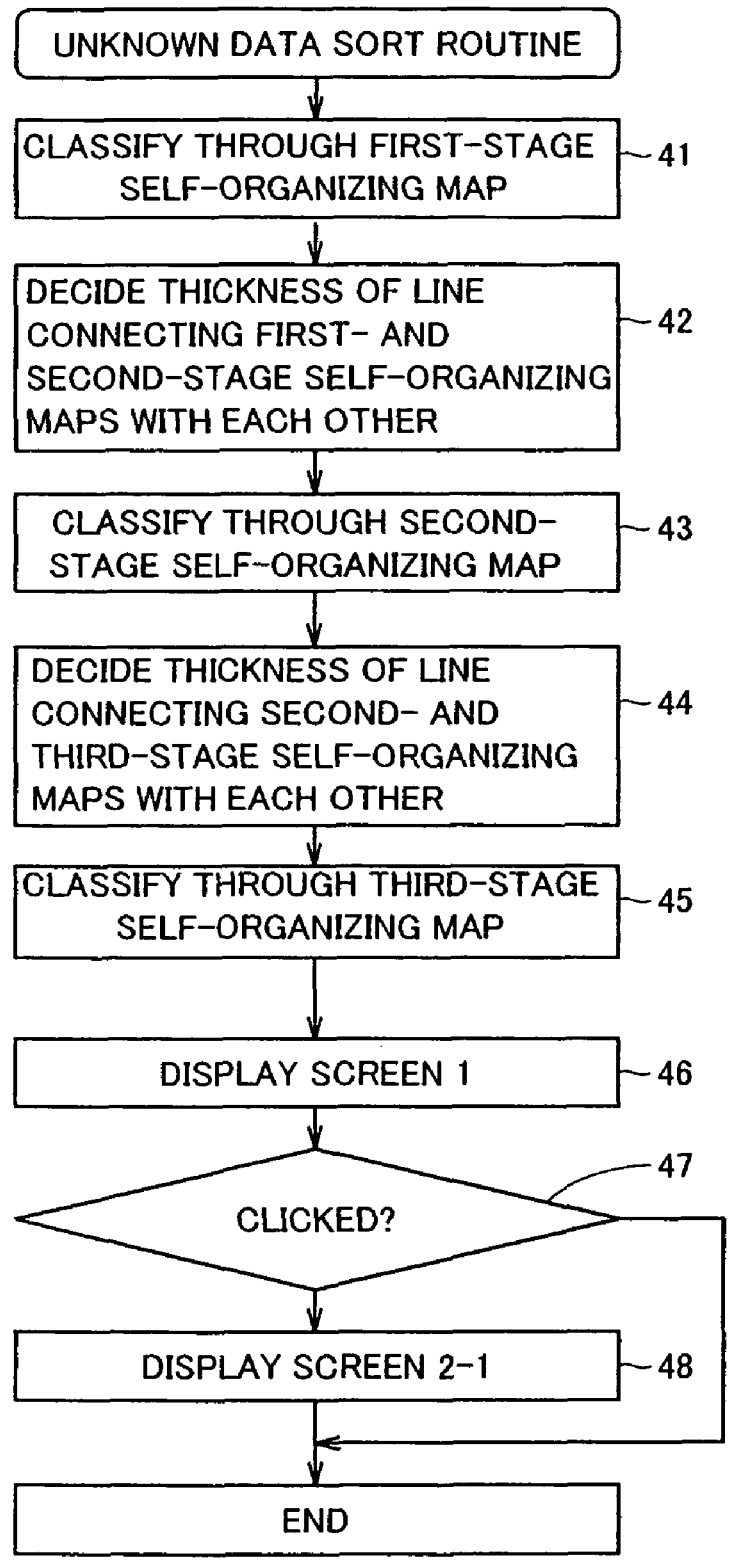
FIG. 8 is a flow chart for illustrating an unknown data classify routine in the data classification supporting method according to the embodiment of the present invention.

Thereafter the control part decides the thicknesses of lines connecting the first-stage self-organizing map 103a and second-stage self-organizing maps 103b with each other at a step 42 shown in FIG. 8 on the basis of the possibility proportions calculated at the step 54 shown in FIG. 9. More specifically, the control part decides the thicknesses to be increased as the possibility proportions are increased. Then, the control part classifys the specimen data (unknown data) with the second-stage self-organizing maps 103b at a step 43 shown in FIG. 8. At this step, the control part performs processing similar to the aforementioned classifying (see FIG. 9) and the aforementioned self-organizing map creation (see FIG. 10). In this classifying, the control part creates three self-organizing maps 103b of groups A, B and C corresponding to three classes (classification areas) A, B and C displayed on the first-stage self-organizing map 103a.

After classifying the specimen data and creating the self-organizing map on the second-stage self-organizing maps 103b, the control part decides the thicknesses of lines connecting the second-stage self-organizing maps 103b and third-stage self-organizing maps 103c with each other at a step 44 shown in FIG. 8 on the basis of the possibility proportions calculated at the step 54 shown in FIG. 9. Thereafter the control part classifys the specimen data (unknown data) on the third-stage self-organizing maps 103c at a step 45 shown in FIG. 8. At this step, the control part performs processing similar to the aforementioned classifying (see FIG. 9) and the aforementioned self-organizing map creation (see FIG. 10). In this classifying, the control part creates three pairs of (six in total) self-organizing maps 103c in correspondence to the pairs of classes (classification areas) displayed on the three second-stage self-organizing maps 103b of the groups A, B and C respectively. Then, the control part tree-displays (hierarchically displays) the first-, second- and third-stage self-organizing maps 103a, 103b and 103c on the analytical result screen (screen 1) at a step 46 shown in FIG. 8, as shown in FIG. 1. When tree-displaying (hierarchically displaying) the self-organizing maps 103a, 103b and 103c, the control part numerically displays the possibility proportions in the vicinity of the lines connecting the first- and second-stage self-organizing maps 103a and 103b with each other and those connecting the second- and third-stage self-organizing maps 103b and 103c with each other respectively.

Thus, the user can easily visually recognize the possibility proportions of the respective self-organizing maps 103a, 103b and 103c.

As to the details of the aforementioned tree-displayed self-organizing maps 103, the control part first displays the overall first-stage self-organizing map 103a having the three types of classification areas A, B and C. Then, the control part displays the three second-stage self-organizing maps 103b of the group A having the possibility proportion of 0% with classification areas A1 and A2, the group B having the possibility proportion of 10% with classification areas B1 and B2 and the group C having the possibility proportion of 90% with classification areas C1 and C2. Thus, the control part displays not only the second-stage self-organizing map 103b of the group C corresponding to the classification area C1 to which the minimum cell 1 belongs but also the second-stage self-organizing maps 103b of the groups A and B corresponding to the classification areas A and B to which the minimum cell 1 does not belong. Thus, the user can easily recognize that a result of classifying (result of classifying of the group B) other than that according to the group C may be obtained. The second-stage self-organizing map 103b of the group A having the possibility proportion of 0% is divided into the third-stage self-organizing maps 103c of the groups. A1 and A2 having possibility proportions of 0%. The second-stage self-organizing map 103b of the group B having the possibility proportion of 10% is divided into the third-stage self-organizing maps 103c of the groups B1 and B2 having possibility proportions of 10% and 0% respectively. Further, the second-stage self-organizing map 103b of the group C having the possibility proportion of 90% is divided into the third-stage self-organizing maps 103c of the groups C1 and C2 having possibility proportions of 90% and 0% respectively.

Then, the control part determines whether or not the user clicks the third-stage self-organizing map 103c of the group C1, for example, of the self-organizing maps 103 on the analytical result screen (screen 1) shown in FIG. 1 at a step 47 shown in FIG. 8. If the user clicks the third-stage self-organizing map 103c of the group C1, the control part displays the analytical detail popup screen (screen 2-1) shown in FIG. 2.

Final disease possibility proportions displayed on the disease possibility proportion display part 104 and under the corresponding third-stage self-organizing maps 103c on the screen 1 shown in FIG. 1 are described with reference to FIGS. 1 and 2. Diseases (3) and (4) belonging to the third-stage self-organizing map 103c of the group C1 have possibility proportions of 89% and 1% respectively. Further, diseases (8) and (9) belonging to the third-stage self-organizing map 103c of the group B1 have possibility proportions of 7% and 3% respectively. More specifically, the minimum cell 1 closest to the specimen data (unknown data) and the similar cells 2 secondly to eleventhly close to the specimen data (unknown data) are present in the class (classification area) 11 (unhatched (blank) areas) indicating the disease (3) as shown in the enlarged diagram (see FIG. 2) of the third-stage self-organizing map 103c of the group C1, and hence the disease (3) corresponding to the class 11 has the large possibility proportion of 89% while the disease (4) corresponding to the class 12 (hatched areas) to which the minimum cell 1 and the similar cells 2 do not belong has the small possibility proportion of 1%. In the third-stage self-organizing map 103c of the group B1 (see FIG. 1) having the possibility proportion of 10%, the first class (classification area) 13 in which the minimum cell 1 closest to the unknown data and the similar cells 2 secondly to eleventhly close to the unknown data are present corresponds to the disease (8) having the possibility proportion of 7% while the second class (classification area) 14 in which the remaining ones of the similar cells 2 secondly to eleventhly close to the unknown data are present corresponds to the disease (9) having the possibility proportion of 3% smaller than that of the disease (8).

Figure 11:
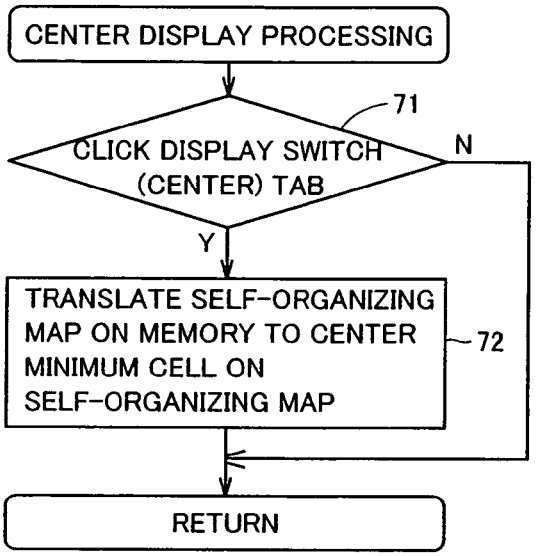
FIG. 11 is a flow chart for illustrating center display processing in the data classification supporting method according to the embodiment of the present invention.

Center display processing on the analytical detail popup screen (screen 2-1) shown in FIG. 2 is described with reference to FIGS. 2, 3 and 11. The control part determines whether or not the user clicks the display switch (center) tab 107 on the analytical detail popup screen (screen 2-1) shown in FIG. 2 at a step 71 shown in FIG. 11. If the user clicks the display switch (center) tab 107, the control part moves the self-organizing map on the memory to center the minimum cell 1, displayed on the lower right end of the self-organizing map of the analytical detail popup screen (screen 2-1) shown in FIG. 2, on the self-organizing map. Thus, the control part switches the display for arranging the minimum cell 1 at the center of the self-organizing map as shown in the analytical detail popup screen (screen 2-2) of FIG. 3. In order to switch the center display shown in FIG. 3 to the standard display shown in FIG. 2, the user clicks a display switch (standard) tab 108 shown in FIG. 3.

Figure 3:
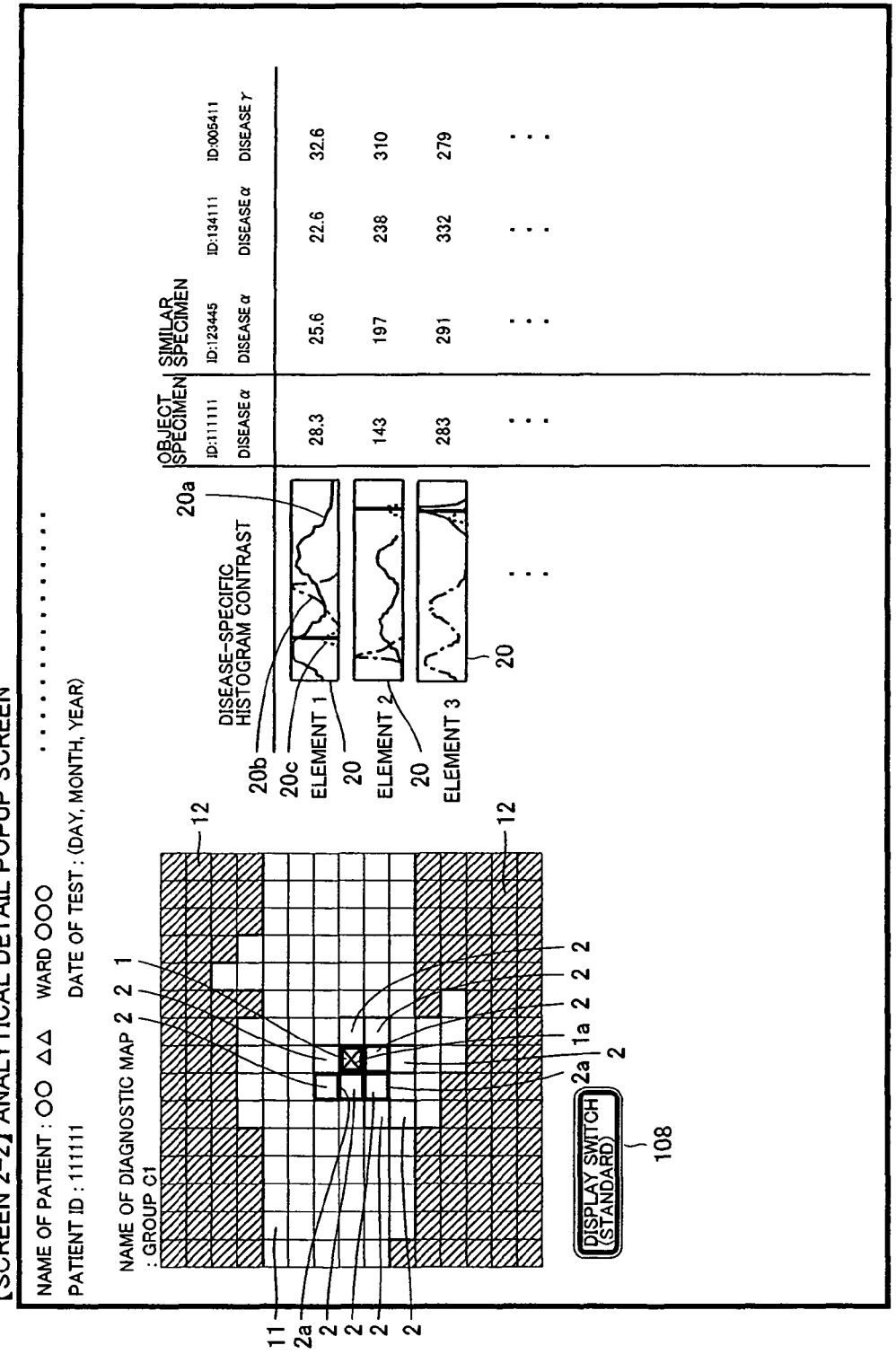
FIG. 3 illustrates another analytical detail screen (center display) (screen 2-2) of the analytical result screen shown in FIG. 1.

Processing of creating the histograms 20 shown in FIGS. 2 and 3 is described with reference to FIGS. 12 and 13. In order to create the histograms 20, the control part reads the unknown data, compares the unknown data with the cell vector data and decides the minimum and similar cells 1 and 2 at steps 81 to 83 shown in FIG. 12, similarly to the steps 51 to 53 for the self-organizing map classifying shown in FIG. 9. Thereafter the control part creates histograms 20a and 20b of the two classes (classification areas) 11 and 12 every element on the basis of learning data of the two classes (classification areas) 11 and 12 of the self-organizing maps displayed on the analytical detail popup screens (screens 2-1 and 2-2) shown in FIGS. 2 and 3. FIGS. 2 and 3 show the histograms 20a and 20b of the classes (classification areas) 11 and 12 with solid and one-chain dot lines respectively. Thereafter the control part creates histograms 20c (see FIGS. 2 and 3) of the minimum and similar cells 1 and 2 every element on the basis of the learning data included in the minimum and similar cells 1 and 2 respectively at a step 85 shown in FIG. 12. FIGS. 2 and 3 show the histograms 20c of the minimum and similar cells 1 and 2 with dotted lines.

Figure 12:
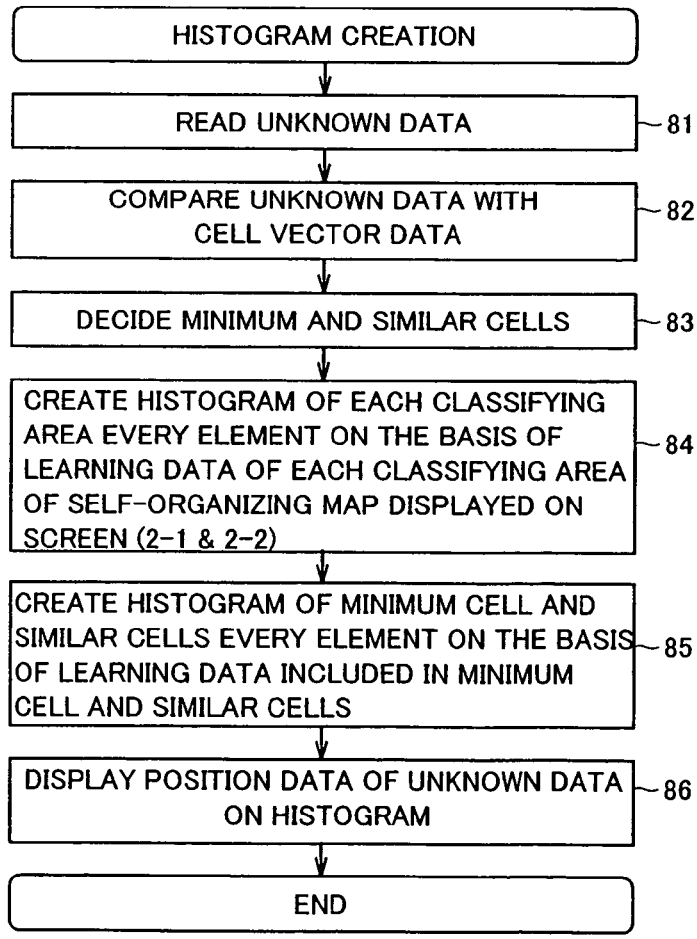
FIG. 12 is a flow chart for illustrating histogram creation in the data classification supporting method according to the embodiment of the present invention.

Thereafter the control part shows position data of the unknown data (specimen data) with vertical solid lines (see FIGS. 2 and 3) on the histograms 20a to 20c at a step 86 shown in FIG. 12. Thus, the control part creates the histograms 20 shown in FIGS. 2 and 3. At the steps 84 and 85, the control part creates the histograms 20a to 20c as to only the cells having learning data 3 on the basis of the learning data 3 since there are cells having the learning data 3 and those having no learning data 3 as shown in FIG. 13.

It is understood from the histograms 20 shown in FIGS. 2 and 3 that the unknown data (specimen data) shown by the vertical solid lines is located in the vicinity of peaks of the histograms 20a of the solid lines created on the basis of the learning data of the classification area (class) 11 as to all elements. It is also understood that the histograms 20c of the dotted lines created on the basis of the learning data of the minimum and similar cells 1 and 2 also overlap with the vertical solid lines indicating the unknown data (specimen data) as to all elements. It is further understood that the unknown data (specimen data) indicated by the vertical solid lines does not overlap with the histograms 20b of the one-dot chain lines created on the basis of the learning data of the classification area (class) 12 as to all elements. Thus, it is inferable that the self-organizing map 103b of the group C1 shown in FIGS. 2 and 3 is correct. Further, the control part displaying the histograms 20 every element can compare the unknown data (specimen data) and the histograms 20 with each other every element. Thus, it is possible to more correctly visually recognize the relation between the unknown data and the similar specimens.

The screens 2-1 and 2-2 shown in FIGS. 2 and 3 display vector element values of the respective elements of the object specimen (unknown data) corresponding to the histograms 20 of the respective elements. Further, the control part successively displays vector element values of three learning data from that closest to the specimen data (unknown data) among those of the minimum and similar cells 1 and 2 having learning data.

According to this embodiment, as hereinabove described, the control part displays the minimum cell mark 1a indicating the minimum cell 1 having the cell vector data closest to the unknown data (specimen data) and the similar cell marks 2a indicating the similar cells 2 having the cell vector data secondly to nthly (eleventhly) close to the unknown data on the self-organizing map so that the minimum cell 1 having the cell vector data closest to the unknown data (specimen data) and the similar cells 2 having the cell vector data secondly to nthly (eleventhly) close to the unknown data can be easily visually recognized.

Further, the control part indicates the minimum cell mark 1a and the similar cell marks 2a with different shapes (□ and □) respectively so that the minimum cell mark 1a and the similar cell marks 2a can be easily visually distinguished from each other.

In addition, the control part varies the thicknesses of the lines forming the similar cell marks 2a with the distances to the unknown data (specimen data) so that which one of the similar cells 2 is close can be easily visually recognized.

According to this embodiment, the control part renders the display of the self-organizing map to center the minimum cell mark 1a and the similar cell marks 2a on the self-organizing map, whereby the relation between the minimum cell mark 1a and the similar cell marks 2a located around the same can be more easily visually recognized when the minimum cell mark 1a and the similar cell marks 2a are centered on the self-organizing map.

Further, the control part displays the self-organizing maps 103 along with the possibility proportions (disease possibility proportions) belonging to the classification areas on the analytical result screen (screen 1) shown in FIG. 1, whereby the user can easily recognize to which disease the unknown data corresponds with what degree of possibility.

In addition, the control part displays the possibility proportions with the lines of various thicknesses on the tree-displayed self-organizing maps 103 so that the possibility proportions can be easily visually recognized.

According to the aforementioned embodiment, the control part displays the histograms 20 along with the self-organizing maps on the analytical detail popup screens (screens 2-1 and 2-2) shown in FIGS. 2 and 3 so that the user can easily infer whether or not the classifying according to the self-organizing maps is really correct. In other words, the user can easily infer whether or not the self-organizing map 103b of the group C1 shown in FIGS. 2 and 3 is correct by comparing the unknown data (specimen data) shown by the vertical solid lines and the histograms 20a, 20b and 20c of the solid, one-chain dot and dotted lines created on the basis of the learning data of the classification area (class) 11 to which the minimum cell 1 belongs, the learning data of the classification area (class) 12 and the learning data of the minimum cell 1 and the similar cells 2 with each other as to all elements.

According to the aforementioned embodiment, the control part displays the histograms 20 every element so that the unknown data (specimen data) and the histograms 20 can be compared with each other every element, whereby the relation between the unknown data and the similar specimens can be more correctly visually recognized.

According to the aforementioned embodiment, the control part numerically displays the unknown data (specimen data) and the similar specimen data along with the histograms 20, whereby the relation between the unknown data (specimen data) and the similar specimens can be numerically recognized.

According to this embodiment, the control part displays the final disease possibility proportions belonging to the classification areas (disease names) in the disease possibility proportion display part 104 and under the corresponding third-stage self-organizing maps 103c along with the self-organizing maps 103 on the analytical result screen (screen 1) shown in FIG. 1, whereby the user can easily recognize to which disease the unknown data corresponds with what degree of possibility.

According to this embodiment, the control part displays the possibility proportions with the lines having various thicknesses on the tree-displayed self-organizing maps 103, whereby the possibility proportions can be easily visually recognized. Further, the control part numerically displays the possibility proportions in the vicinity of the lines showing the possibility proportions, whereby the user can easily visually recognize the possibility proportions of the respective self-organizing maps 103.

According to this embodiment, as hereinabove described, the control part displays not only the second-stage self-organizing map 103b of the group C corresponding to the classification area C of the first-stage self-organizing map 103a to which the minimum cell 1 belongs but also the second-stage self-organizing maps 103b of the groups A and B corresponding to the classification areas A and B to which the minimum cell 1 does not belong so that the user can easily recognize that a result of classifying (result of classifying of the group B) other than that according to the group C may be obtained. Thus, the user can recognize that no correct result of classifying may be obtained.

Although the present invention has been described and illustrated in detail, it is clearly understood that the same is by way of illustration and example only and is not to be taken by way of limitation, the spirit and scope of the present invention being limited only by the terms of the appended claims.

For example, while the control part classifys the unknown data with the self-organizing maps (SOM) employed as examples of the classification map according to the present invention in the aforementioned embodiment, the present invention is not restricted to this but is also applicable to a case of classifying unknown data with a classification map other than a self-organizing map.

While the shapes X and □ are employed as the minimum cell mark 1a and the similar cell marks 2a respectively in the aforementioned embodiment, the present invention is not restricted to this but the minimum cell mark 1a and the similar cell marks 2a may alternatively be shown by other shapes. Further, the colors of the minimum cell mark 1a and the similar cell marks 2a may be differentiated from each other.

While the thicknesses of the similar cell marks 2a are varied for indicating the degrees of closeness of the similar cell marks 2a to the unknown data in the aforementioned embodiment, the present invention is not restricted to this but the degrees of closeness of the similar cell marks 2*a* to the unknown data may alternatively be shown by another method.

Figure 13:
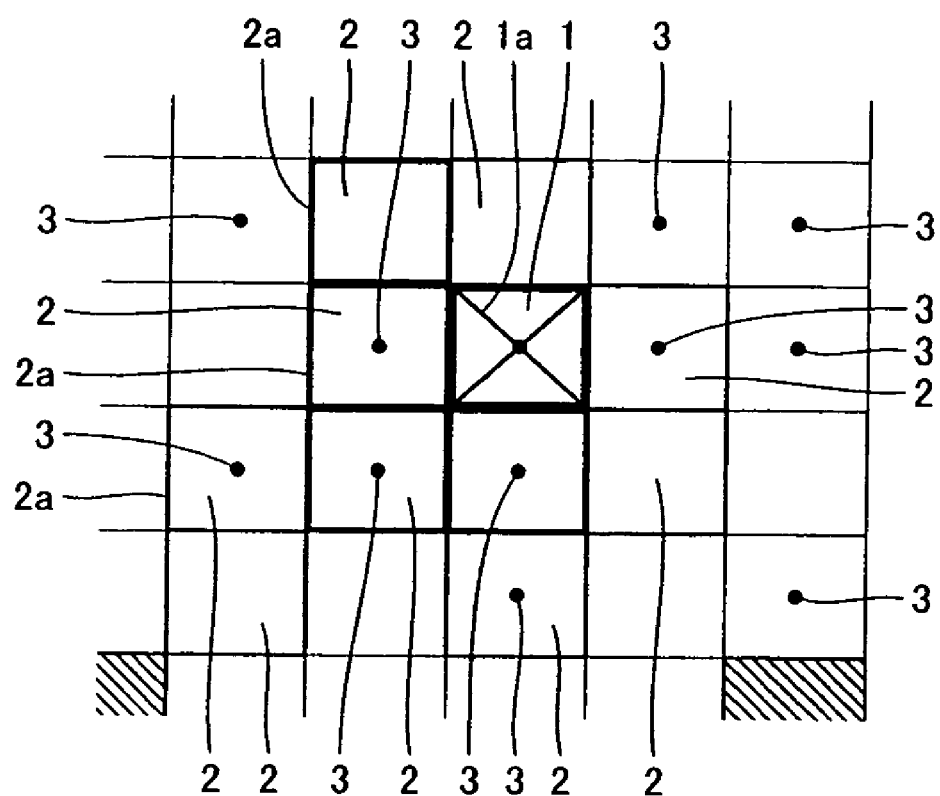
FIG. 13 is a diagram for illustrating cells having learning data and those having no learning data.

While no learning data are displayed on the self-organizing maps shown in FIGS. 1 to 3 in the aforementioned embodiment, the present invention is not restricted to this but learning data may alternatively be displayed on a self-organizing map, as shown in FIG. 13. In this case, cells having learning data and those having no learning data can be easily visually distinguished from each other.

While the classification areas (classes) on the self-organizing maps shown in FIGS. 2 and 3 are rendered visually distinguishable in response to presence/absence of hatching (slant lines) in the aforementioned embodiment, the colors of the classification areas (classes) on the self-organizing maps are preferably differentiated from each other on an actual color display screen.

While the screens 2-1 and 2-2 (see FIGS. 2 and 3) are displayed when the user clicks the self-organizing map 103*c* of the group C1 on the screen 1 shown in FIG. 1 in the aforementioned embodiment, the present invention is not restricted to this but screens similar to the screens 2-1 and 2-2 (see FIGS. 2 and 3) can be displayed also when the user clicks another self-organizing map (e.g., the self-organizing map 103*c* of the group B1) on the screen 1. In this case, the screen 2-1 (or 2-2) displays an enlarged view of the self-organizing map clicked on the screen 1, histograms, specimen data and similar specimen data.

While the specimen data (unknown data) is read from the database in the aforementioned embodiment, the present invention is not restricted to this but the user may alternatively manually input the specimen data (unknown data) from the computer terminal. When the data classification supporting method according to the aforementioned embodiment is provided to the user as a WEB service or the like, the computer terminal or the server may receive a message including the specimen data (unknown data) transmitted onto a network.

While the self-organizing maps created by the prescribed facility preserved in the server database (server DB) are selected and employed in the aforementioned embodiment, the present invention is not restricted to this but self-organizing maps created by a prescribed facility may be downloaded from a prescribed homepage on the Internet.

While the histograms are employed as examples of the first to third distribution charts according to the present invention in the aforementioned embodiment, the present invention is not restricted to this but distribution charts other than histograms may alternatively be employed.

While the histograms of the respective classification areas, those of the minimum and similar cells and those of the unknown data are successively created in the histogram creation processing shown in FIG. 12 in the aforementioned embodiment, the present invention is not restricted to this but the order of creating the histograms is properly changeable.

While the unknown data is employed as the value $E_i$ in the expression (1) for calculating the possibility ($E_{ic}=K_c/K$) that the unknown data belongs to each classification area in the aforementioned embodiment, the present invention is not restricted to this but the possibility ($E_{ic}=K_c/K$) that the unknown data belongs to each classification area may alternatively be calculated by employing the cell vector data of the minimum cell 1 as the value $E_i$ in the expression (1).

While the possibility ($E_{ic}=K_c/K$) that the unknown data belongs to each classification area is calculated with the values $K$ and $K_c$ obtained in the expressions (1) and (2) including the Gaussian function in the aforementioned embodiment, the present invention is not restricted to this but the possibility ($E_{ic}=K_c/K$) that the unknown data belongs to each classification area may alternatively be calculated through other expressions. In this case, it is preferable to employ expressions including such a function that the possibility is increased as the inter-vector distance between the unknown data and the learning data is reduced. A delta function or the like may conceivably be employed in place of the Gaussian function.

While the possibility proportions are displayed with both of the thicknesses of the lines and the numerical values on the tree-displayed self-organizing maps 103 in the aforementioned embodiment, the present invention is not restricted to this but the possibility proportions may alternatively be displayed with either the thicknesses of the lineclassifyhe numerical values, or by another method.

While both of the decision of the minimum and similar cells 1 and 2 and the calculation of the possibility proportions are performed in the aforementioned embodiment, the present invention is not restricted to this but only the possibility proportions can alternatively be calculated without deciding the minimum an similar cells 1 and 2 by employing the unknown data as the value $E_i$ in the expression (1).

What is claimed is:

1. A data classification supporting method for classifying unknown data, the method performed by a computer and comprising:

displaying on a display a selection screen for selecting a classification map from a plurality of classification maps stored in a memory;

wherein each of the classification maps comprises a plurality of classification areas, each of which comprises data sections;

wherein each of the data sections comprises vector data decided based on prescribed learning data;

wherein the classification areas respectively correspond to different diseases; and wherein the learning data comprise clinical data of patients judged by a doctor;

receiving a selection of a classification map in the selection screen;

reading the selected classification map from the memory;

classifying the unknown data into a classification area of the plurality of classification areas based on the classification map read from the memory, wherein the unknown data comprises clinical laboratory data of a patient;

comparing the vector data of each of the data sections with the unknown data;

identifying a data section having the vector data closest to the unknown data as a target data section based on results of the comparing of the vector data and the unknown data;

indicating a position of the target data section on the classification map;

displaying the classification map, wherein the position of the target data section is indicated on the map;

calculating a percentage representing a reliability of a result of the classifying of the unknown data, using the computer, wherein calculating the percentage comprises:

calculating a first value based on either the unknown data or the vector data of the target data section and the learning data corresponding to each data section belonging to the classification area into which the unknown data is classified;

calculating a second value by summating values calculated based on either the unknown data or the vector data of the target data section and the learning data corresponding to each data section belonging to any one of the plurality of classification areas with respect to all of the plurality of classification areas; and
calculating the percentage by obtaining a ratio of the first value to the second value; and
displaying the calculated percentage on the display.

2. The data classification supporting method according to claim 1, wherein the calculating of the percentage is based on the unknown data and the learning data corresponding to the data sections belonging to the classification map.

3. The data classification supporting method according to claim 1, wherein the calculating of the percentage is based on the vector data of the target data section and the learning data corresponding to the data sections belonging to the classification map.

4. The data classification supporting method according to claim 1, wherein the calculating of the percentage comprises calculating a percentage Eic that the unknown data belongs to a classification area c according to an expression:

$$Eic = Kc/K$$

wherein values of Kc and K are obtained as follows:

$$Kc = \sum_{j=1}^{Nc} \frac{1}{Nc} \cdot f(|Ei - Scj|)$$

$$K = \sum_{c=1}^{M} Kc$$

and wherein Nc represents number of learning data in the classification area c, M represents number of the classification areas, Scj represents j-th learning data belonging to the classification area c, Ei represents the unknown data or the vector data of the target data section, and f( ) represents a Gaussian function.

5. The data classification supporting method according to claim 1, wherein the classification map comprises a self-organizing map.

6. A computer readable storage medium comprising a program for classifying unknown data, wherein the program enables the computer to perform operations comprising:
providing a classification map comprising a plurality of classification areas each of which comprises data sections each having vector data decided based on prescribed learning data, the classification areas respectively corresponding to different diseases and the learning data comprising clinical data of patients judged by a doctor;
classifying the unknown data into a classification area of the plurality of classification areas, the unknown data comprising clinical laboratory data of a patient;
comparing the vector data of each of the data sections with the unknown data;
identifying a data section having the vector data closest to the unknown data as a target data section based on results of the comparing of the vector data and the unknown data;
indicating a position of the target data section on the classification map;
displaying the classification map, wherein the position of the target data section is indicated on the map;
calculating a percentage representing a reliability of a result of the classifying of the unknown data, wherein calculating the percentage comprises:
calculating a first value based on either the unknown data or the vector data of the target data section and the learning data corresponding to each data section belonging to the classification area into which the unknown data is classified;
calculating a second value by summating values calculated based on either the unknown data or the vector data of the target data section and the learning data corresponding to each data section belonging to any one of the plurality of classification areas with respect to all of the plurality of classification areas; and
calculating the percentage by obtaining a ration of the first value to the second value; and
displaying the calculated percentage.

7. A data classification supporting apparatus for classifying unknown data, comprising:
a programmed computer;
providing means for providing a classification map comprising a plurality of classification areas each of which comprises data sections each having vector data decided based on prescribed learning data, the classification areas respectively corresponding to different diseases and the learning data comprising clinical data of patients judged by a doctor;
classifying means for classifying the unknown data into a classification area of the plurality of classification areas, the unknown data comprising clinical laboratory data of a patient;
comparing means for comparing the vector data of each of the data sections with the unknown data;
identifying means for identifying a data section having the vector data closest to the unknown data as a target data section based on results of the comparing of the vector data and the unknown data;
indicating means for indicating a position of the target data section on the classification map;
displaying means for displaying the classification map, wherein the position of the target data section is indicated on the map;
percentage calculation means for calculating a percentage representing a reliability of a classification result by the classifying means, wherein the percentage calculating means comprises:
means for calculating a first value based on either the unknown data or the vector data of the target data section and the learning data corresponding to each data section belonging to the classification area into which the unknown data is classified;
means for calculating a second value by summating values calculated based on either the unknown data or the vector data of the target data section and the learning data corresponding to each data section belonging to any one of the plurality of classification areas with respect to all of the plurality of classification areas; and
means for calculating the percentage by obtaining a ratio of the first value to the second value; and
display means for displaying the calculated percentage.

8. A data classification supporting method for classifying unknown data, the method performed by a computer and comprising:
displaying on a display a selection screen for selecting a classification map from a plurality of classification maps stored in a memory;
wherein each of the classification maps comprises a plurality of classification areas, each of which comprises data sections;

wherein each of the data sections comprises vector data decided based on prescribed learning data;

wherein the classification areas respectively correspond to different diseases; and wherein the learning data comprise clinical data of patients judged by a doctor;

receiving a selection of a classification map in the selection screen;

reading the selected classification map from the memory;

classifying the unknown data into a classification area of the plurality of classification areas based on the classification map read from the memory, wherein the unknown data comprises clinical laboratory data of a patient;

comparing the vector data of each of the data sections with the unknown data;

identifying a data section having the vector data closest to the unknown data as a target data section based on results of the comparing of the vector data and the unknown data;

indicating a position of the target data section on the classification map;

displaying the classification map, wherein the position of the target data section is indicated on the map;

calculating a percentage representing a reliability of a result of the classifying of the unknown data, using the computer, wherein calculating the percentage comprises:

calculating a percentage Eic that the unknown data belongs to a classification area c according to an expression:

$Eic = Kc/K$ wherein values of Kc and K are obtained as follows:

$$Kc = \sum_{j=1}^{Nc} \frac{1}{Nc} \cdot f(|Ei - Scj|)$$

$$K = \sum_{c=1}^{M} Kc$$

and wherein Nc represents number of learning data in the classification area c, M represents number of the classification areas, Scj represents j-th learning data belonging to the classification area c, Ei represents the unknown data or the vector data of the target data section, and f( ) represents a Gaussian function; and displaying the calculated percentage on the display.

9. A computer readable storage medium comprising a program for classifying unknown data, wherein the program enables the computer to perform operations comprising:

providing a classification map comprising a plurality of classification areas each of which comprises data sections each having vector data decided based on prescribed learning data, the classification areas respectively corresponding to different diseases and the learning data comprising clinical data of patients judged by a doctor;

classifying the unknown data into a classification area of the plurality of classification areas, the unknown data comprising clinical laboratory data of a patient;

comparing the vector data of each of the data sections with the unknown data;

identifying a data section having the vector data closest to the unknown data as a target data section based on results of the comparing of the vector data and the unknown data;

indicating a position of the target data section on the classification map;

displaying the classification map, wherein the position of the target data section is indicated on the map;

calculating a percentage representing a reliability of a result of the classifying of the unknown data, wherein calculating the percentage comprises:

calculating a percentage Eic that the unknown data belongs to a classification area c according to an expression:

$Eic = Kc/K$ wherein values of Kc and K are obtained as follows:

$$Kc = \sum_{j=1}^{Nc} \frac{1}{Nc} \cdot f(|Ei - Scj|)$$

$$K = \sum_{c=1}^{M} Kc$$

and wherein Nc represents number of learning data in the classification area c, M represents number of the classification areas, Scj represents j-th learning data belonging to the classification area c, Ei represents the unknown data or the vector data of the target data section, and f( ) represents a Gaussian function; and displaying the calculated percentage.

10. A data classification supporting apparatus for classifying unknown data, comprising:

a programmed computer;

providing means for providing a classification map comprising a plurality of classification areas each of which comprises data sections each having vector data decided based on prescribed learning data, the classification areas respectively corresponding to different diseases and the learning data comprising clinical data of patients judged by a doctor;

classifying means for classifying the unknown data into a classification area of the plurality of classification areas, the unknown data comprising clinical laboratory data of a patient;

comparing means for comparing the vector data of each of the data sections with the unknown data;

identifying means for identifying a data section having the vector data closest to the unknown data as a target data section based on results of the comparing of the vector data and the unknown data;

indicating means for indicating a position of the target data section on the classification map;

displaying means for displaying the classification map, wherein the position of the target data section is indicated on the map;

percentage calculation means for calculating a percentage representing a reliability of a classification result by the classifying means, wherein the percentage calculating means comprises:

means for calculating a percentage Eic that the unknown data belongs to a classification area c according to an expression:

$Eic = Kc/K$ wherein values of Kc and K are obtained as follows:

$$Kc = \sum_{j=1}^{Nc} \frac{1}{Nc} \cdot f(|Ei - Scj|)$$

$$K = \sum_{c=1}^{M} Kc$$

and wherein Nc represents number of learning data in the classification area c, M represents number of the classification areas, Scj represents j-th learning data belonging to the classification area c, Ei represents the unknown data or the vector data of the target data section, and f( ) represents a Gaussian function; and display means for displaying the calculated percentage.

* * * * *

UNITED STATES PATENT AND TRADEMARK OFFICE
CERTIFICATE OF CORRECTION

PATENT NO. : 7,877,238 B2
APPLICATION NO. : 10/938116
DATED : January 25, 2011
INVENTOR(S) : Kiyoaki Watanabe et al.

It is certified that error appears in the above-identified patent and that said Letters Patent is hereby corrected as shown below:

In the Claims

In column 24, claim 6, line 12, after "percentage by obtaining a" replace "ration" with --ratio--.

Signed and Sealed this
Nineteenth Day of April, 2011

David J. Kappos
*Director of the United States Patent and Trademark Office*